(12) United States Patent
Bann

(10) Patent No.: US 7,731,979 B2
(45) Date of Patent: Jun. 8, 2010

(54) PROTECTIVE ANTIGEN HAVING FLUORINATED HISTIDINE RESIDUES

(75) Inventor: James G. Bann, Wichita, KS (US)

(73) Assignee: Wichita State University, Wichita, KS (US)

( * ) Notice: Subject to any disclaimer, the term of this patent is extended or adjusted under 35 U.S.C. 154(b) by 18 days.

(21) Appl. No.: 11/939,249

(22) Filed: Nov. 13, 2007

(65) Prior Publication Data

US 2009/0123458 A1  May 14, 2009

(51) Int. Cl.
*A61K 39/07* (2006.01)
*A61K 51/00* (2006.01)
*A61K 39/38* (2006.01)
*A61K 39/02* (2006.01)
*A61K 38/00* (2006.01)

(52) U.S. Cl. ............... 424/246.1; 424/1.89; 424/184.1; 424/234.1; 424/236.1; 514/2

(58) Field of Classification Search ....................... None
See application file for complete search history.

(56) References Cited

OTHER PUBLICATIONS

Zhou et al (The 40th Midwest Region Meeting, BIOMED Poster Session, Oct. 26-29, 2005, acs.confex.com).*
Zhou (SOAR at Wichita State University Libraries), http://hdl.handle.net/10057/560, issued date Jul. 2006).*
Bowie et al (Science, 1990, 257:1306-1310).*
Zhou, Influence of Fluorohistidine on Pore Formation in the Anthrax Protective Antigen, (SOAR at Wichita State University Libraries), http://hdl.handle.net/10057/560, issued date Jul. 2006 publically available Jul. 2007).*
Conference Summary, (Emerging Infectious Diseases, vol. 8, No. 2, Feb. 2002, p. 222-225).*
Bann, *Probing the role of histidine in the anthrax toxin protective antigen with 2-fluoro-histidine*, PowerPoint Presentation, 3$^{rd}$ Annual RCE National meeting in New York City (Mar. 27, 2006).

* cited by examiner

*Primary Examiner*—Vanessa L. Ford
(74) *Attorney, Agent, or Firm*—Stinson Morrison Hecker LLP

(57) ABSTRACT

The unnatural amino acid analogue 2-fluorohistidine (2-FHis) was incorporated into protective antigen to produce a protein which resists protonation at physiological pH by reducing the side-chain pKa. The protein structure was unperturbed by the incorporation of fluorinated histidine residues, and the heptameric $(2\text{-FHisPA}_{63})_7$ could form ion conducting channels, and bind to the PA-binding domain of LF ($LF_N$), but translocation of $LF_N$ in planar lipid bilayers was blocked. Further, while $(2\text{-FHisPA}_{63})_7$ could bind to host cells and in vitro to the host cellular receptor, pore formation in the presence of the receptor was blocked, and $LF_N$-DTA mediated cytotoxicity in CHO-K1 cells was blocked. The modified PA is useful as both a vaccine and an antitoxin, providing epitopes for the production of antibodies against PA, but preventing key steps in pathogenesis (pore formation, translocation).

6 Claims, 12 Drawing Sheets

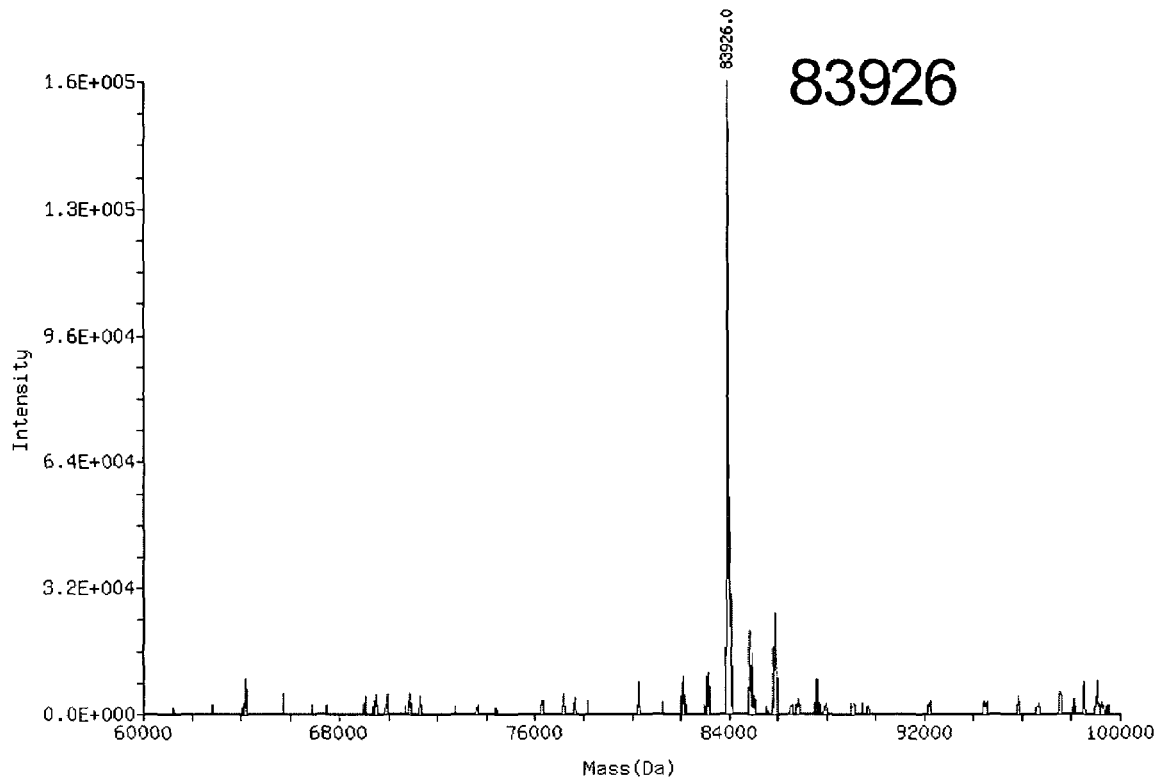

FIG 1B

Figure 1A:
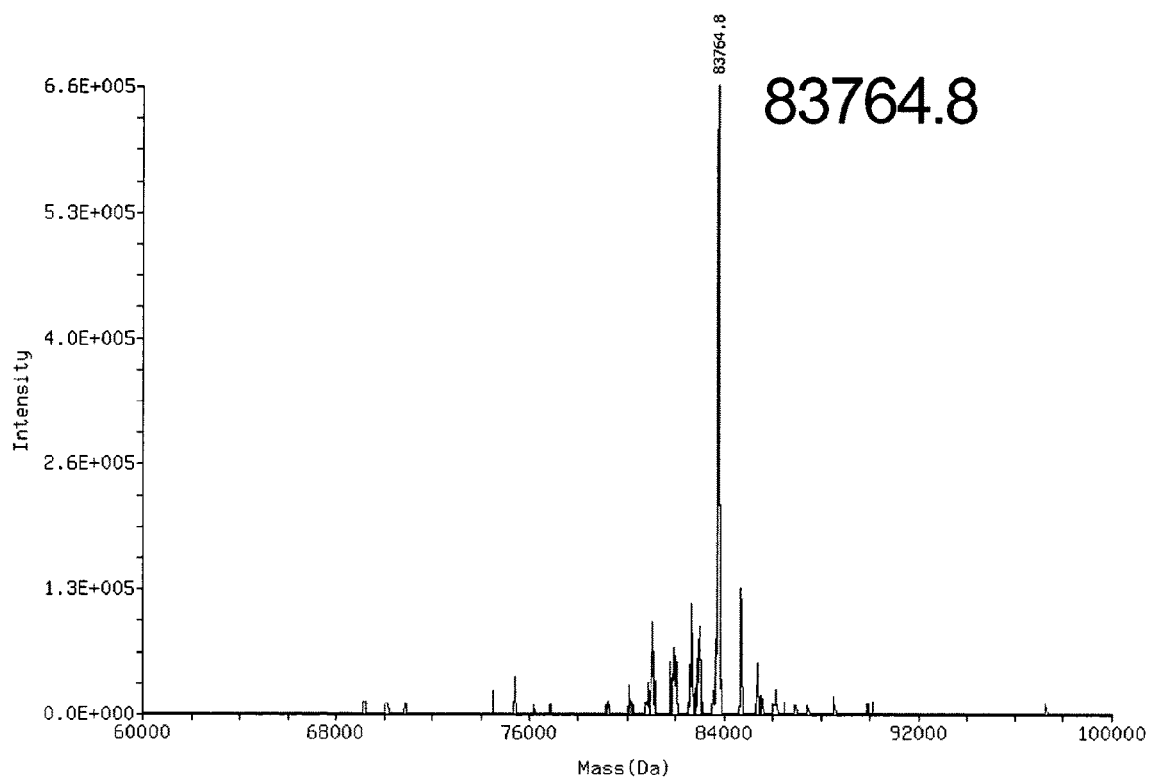

MKYLLPTAAA GLLLLAAQPA MAMDIGINSD PMEVKQENRL LNESESSSQG
LLGYYFSDLN FQAPMVVTSS TTGDLSIPSS ELENIPSENQ YFQSAIWSGF
IKVKKSDEYT FATSADNHVT MWVDDQEVIN KASNSNKIRL EKGRLYQIKI
QYQRENPTEK GLDFKLYWTD SQNKKEVISS DNLQLPELKQ KSSNSRKKRS
TSAGPTVPDR DNDGIPDSLE VEGYTVDVKN KRTFLSPWIS NIHEKKGLTK
YKSSPEKWST ASDPYSDFEK VTGRIDKNVS PEARHPLVAA YPIVHVDMEN
IILSKNEDQS TQNTDSQTRT ISKNTSTSRT HTSEVHGNAE VHASFFDIGG
SVSAGFSNSN SSTVAIDHSL SLAGERTWAE TMGLNTADTA RLNANIRYVN
TGTAPIYNVL PTTSLVLGKN QTLATIKAKE NQLSQILAPN NYYPSKNLAP
IALNAQDDFS STPITMNYNQ FLELEKTKQL RLDTDQVYGN IATYNFENGR
VRVDTGSNWS EVLPQIQETT ARIIFNGKDL NLVERRIAAV NPSDPLETTK
PDMTLKEALK IAFGFNEPNG NLQYQGKDIT EFDFNFDQQT SQNIKNQLAE
LNATNIYTVL DKIKLNAKMN ILIRDKRFHY DRNNIAVGAD ESVVKEAHRE
VINSSTEGLL LNIDKDIRKI LSGYIVEIED TEGLKEVIND RYDMLNISSL
RQDGKTFIDF KKYNDKLPLY ISNPNYKVNV YAVTKENTII NPSENGDTST
NGIKKILIFS KKGYEIG

FIG. 1C

SEQUENCE LISTING

```
<160> NUMBER OF SEQ ID NOS: 7

<210> SEQ ID NO 1
<211> LENGTH: 764
<212> TYPE: PRT
<213> ORGANISM: Bacillus anthracis

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160
```

-continued

```
Phe Lys Leu Tyr Trp Thr Asp Ser Gln Asn Lys Lys Glu Val Ile Ser
            165                 170                 175
Ser Asp Asn Leu Gln Leu Pro Glu Leu Lys Gln Lys Ser Ser Asn Ser
            180                 185                 190
Arg Lys Lys Arg Ser Thr Ser Ala Gly Pro Thr Val Pro Asp Arg Asp
            195                 200                 205
Asn Asp Gly Ile Pro Asp Ser Leu Glu Val Glu Gly Tyr Thr Val Asp
            210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
                260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
            290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
                340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
            370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
                420                 425                 430
Ile Leu Ala Pro Asn Asn Tyr Tyr Pro Ser Lys Asn Leu Ala Pro Ile
            435                 440                 445
Ala Leu Asn Ala Gln Asp Asp Phe Ser Ser Thr Pro Ile Thr Met Asn
450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
                485                 490                 495
Arg Val Arg Val Asp Thr Gly Ser Asn Trp Ser Glu Val Leu Pro Gln
                500                 505                 510
Ile Gln Glu Thr Thr Ala Arg Ile Ile Phe Asn Gly Lys Asp Leu Asn
            515                 520                 525
Leu Val Glu Arg Arg Ile Ala Ala Val Asn Pro Ser Asp Pro Leu Glu
            530                 535                 540
Thr Thr Lys Pro Asp Met Thr Leu Lys Glu Ala Leu Lys Ile Ala Phe
545                 550                 555                 560
Gly Phe Asn Glu Pro Asn Gly Asn Leu Gln Tyr Gln Gly Lys Asp Ile
                565                 570                 575
Thr Glu Phe Asp Phe Asn Phe Asp Gln Gln Thr Ser Gln Asn Ile Lys
```

```
                580                 585                 590
Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760
```

<210> SEQ ID NO 2
<211> LENGTH: 35
<212> TYPE: DNA
<213> ORGANISM: Bacillus anthracis

<400> SEQUENCE: 2
gcaggattta gtaattcgaa ctcaagtacg gtcgc                35

<210> SEQ ID NO 3
<211> LENGTH: 35
<212> TYPE: DNA
<213> ORGANISM: Bacillus anthracis

<400> SEQUENCE: 3
gcgaccgtac ttgagttcga attactaaat cctgc                35

<210> SEQ ID NO 4
<211> LENGTH: 51
<212> TYPE: DNA
<213> ORGANISM: Bacillus anthracis

<400> SEQUENCE: 4
cccgaattca ttaaagagga gaaattaact atgaaatacc tgctgccgac c      51

<210> SEQ ID NO 5
<211> LENGTH: 33
<212> TYPE: DNA
<213> ORGANISM: Bacillus anthracis

<400> SEQUENCE: 5
gggggtacct cagctaatta tcctatctca tag                  33

<210> SEQ ID NO 6
<211> LENGTH: 33
<212> TYPE: DNA

```
-continued

<213> ORGANISM: Homo sapiens

<400> SEQUENCE: 6
ccgcgtccat cctgcagaag agcctttgat ctc                                      33

<210> SEQ ID NO 7
<211> LENGTH: 40
<212> TYPE: DNA
<213> ORGANISM: Homo sapiens

<400> SEQUENCE: 7
ggggatgcgg ccctcagtca acatgactga gctagtatag                               40
```

PROTECTIVE ANTIGEN HAVING FLUORINATED HISTIDINE RESIDUES

STATEMENT REGARDING FEDERALLY SPONSORED RESEARCH OR DEVELOPMENT

The present invention was supported in part by the National Institutes of Health ("NIH") grant U54 AI057160 to the Midwest Regional Center of Excellence for Biodefense and Emerging and Infectious Disease Research ("MRCE") and NIH grant AI22021, and the federal government may have certain rights in the invention.

CROSS-REFERENCE TO RELATED APPLICATIONS

Not applicable.

BACKGROUND OF THE INVENTION

1. Field of the Invention

In general, the invention is directed to compounds derived from protective antigen and methods for the treatment of anthrax and for understanding the mechanisms involved in anthrax infection.

2. Description of Related Art

The etiologic agent of anthrax (*Bacillus anthracis*) is a potential threat as an agent of biowarfare or bioterrorism because exposure to aerosolized *B. anthracis* spores can be lethal to mammals, such as humans. Anthrax toxin is a member of the class of bacterial toxins termed A-B toxins. A-B toxins are composed of two moieties. The A moiety is the enzymic portion of the toxin that catalyzes the toxic effect upon a cytoplasmic target within a target cell. The B moiety binds to a cellular receptor and facilitates the translocation of the A moiety across the cell membrane into the cytoplasm of the cell.

The B moieties of A-B toxins from tetanus, botulinum, diphtheria, and anthrax all form channels in membranes. The A and B moieties of anthrax toxin are secreted from the bacterial cell as distinct polypeptides. The A and B subunits of other A-B toxins are produced as single chain polypeptides or as separate chains that are assembled into oligomeric toxins before release from the bacteria.

The A-B toxin secreted from *Bacillus anthracis* is comprised of the B moiety protective antigen ("PA"), and the A moieties edema factor ("EF"), and lethal factor ("LF"). EF is a calmodulin-dependent adenylate cyclase which may protect the bacteria from destruction by phagocytes. LF is a metalloprotease that can kill macrophages or, at lower concentrations, induce macrophages to overproduce cytokines, possibly resulting in death of the host. PA is a channel forming polypeptide that allows entry of EF and LF across membranes into the cell, a step that is critical for the pathogenesis of anthrax. PA is secreted as a four-domain, 83 kD protein that recognizes on host cells the von-Willebrand factor A domain ("VWA") of two integrin-like receptors: anthrax toxin receptor 1, ("ANTXR1") formerly anthrax toxin receptor-tumor endothelial marker 8, and anthrax toxin receptor 2 ("ANTXR2"), formerly capillary morphogenesis protein 2 ("CMG2"). Binding of PA to the receptor results in the proteolytic cleavage of PA by a furin-like protease on the cell surface, releasing the first 167 amino acid residues of domain 1. Thus, the C-terminal 63 kDa fragment ("$PA_{63}$") remains bound to the cell and the N-terminal 20 kDa fragment ("$PA_{20}$") dissociates from $PA_{63}$. This proteolytic cleavage and subsequent dissociation of $PA_{20}$ confer at least two new properties on $PA_{63}$: (1) the ability to oligomerize into a ring-shaped heptameric sodium dodecyl sulfate ("SDS")-dissociable structure termed prepore and (2) the ability to bind EF and LF, which bind with a stoichiometry of three per heptameric prepore. Binding of PA to the receptor also initiates receptor-mediated endocytosis into an endosomal compartment, which eventually becomes acidified. The low pH within the endosome induces a conformational change in the protective antigen that results in the formation of a membrane spanning channel, and this new conformation of the entire PA heptamer is termed the pore. The pore allows the transport of EF and LF into the cytosol. The exact pH required for pore formation is dependent upon interactions with receptor—in vitro studies indicate that the pH is about 5 if the receptor is ANTXR2, and a slightly higher pH (about 6) if the receptor is ANTXR1. The receptor then dissociates from PA, allowing conformational changes to occur throughout the protein such that PA forms a membrane spanning pore. See generally, Collier, U.S. Published Patent Application No. 2002/0039588 titled "Compounds and methods for the treatment and prevention of bacterial infection," which is incorporated by reference.

The mechanism for this prepore to pore conversion is currently under investigation, but likely involves the protonation of key histidine residues. The transmembrane channel of the pore is comprised of residues 285-340 from domain 2, and may involve the protonation of histidine residues solely within this domain. Since the pH conversion occurs near the histidine pKa (about 6), it has been theorized that histidine protonation may be the trigger for pore formation.

BRIEF SUMMARY OF THE INVENTION

The present invention is directed to novel compositions of matter, and in particular, to PA proteins having one or more modified amino acids which have significantly decreased pKa values compared to the same amino acids in the wild-type PA protein. In a preferred aspect, the modified amino acids comprise one or more histidine residues that have been modified to reduce the pKa. Still more preferably, the histidine residues are modified so that the pKa is less than about 3, 2, or 1.

In one aspect, the pKa of the histidine residues is reduced by fluorinating the histidine residues.

In yet another aspect, the present invention is directed to a PA protein having 1, 2, 3, 4, 5, 6, 7, 8, 9, or 10 of the histidine residues that are fluorinated.

In another aspect, more than about 50%, 60%, 65%, 70%, 75%, 80%, 85%, 90%, or about 95% of the histidine residues are fluorinated.

In yet another aspect, the present invention is directed to a PA protein that is fluorinated at the 2-position, i.e., the histidine residue comprises a 2-fluoro histidine residue, which is shown below:

In yet another aspect, the fluorinated histidine residues are selected from the group consisting of the ten histidine residues in PA, namely His86, His211, His253, His263, His 299, His304, His310, His336, His597, and His616.

In still another aspect, the invention is directed to a pharmaceutical composition comprising the modified PA protein and further comprising an optional therapeutic agent for the treatment of anthrax infection.

In one aspect, the optional therapeutic agent is selected from the group consisting of an antibody against LF, an antibody against EF, and an antibody against PA. In another aspect, the optional therapeutic agent is selected from the group consisting of ciprofloxacin, doxycycline, amoxicillin, chloramphenicol, clindamycin, tetracycline, rifampin, vancomycin, and penicillin G procaine.

In yet another aspect, the present invention is directed to a vaccine for the treatment of anthrax and a method for inducing an immunogenic response and/or protective immunity in a subject comprising the step of administering to the subject an immunogenic composition comprising an immunogenic amount of the modified PA protein. Optionally, the subject is further co-administered a therapeutic agent, including an antibiotic such as ciprofloxacin, doxycycline, amoxicillin, or penicillin G procaine. Thus, according to a related aspect, the present invention relates to a vaccine for preventing and/or treating an anthrax-associated disease or infection.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 shows the ESI-MS analysis of wild-type ("WT") $PA_{83}$ (FIG. 1A) and 2-FHis$PA_{83}$ (FIG. 1B). FIG. 1C shows the amino acid sequence (SEQ ID NO: 1) of the full-length $PA_{83}$ protein _including the pelB leader peptide, which directs the protein for export to the periplasm and is cleaved off to give the mature polypeptide (MW=83748.4 Da). The ESI spectra were acquired on a Finnigan LTQ-FT mass spectrometer.

FIG. 2 shows cytotoxicity as determined by protein synthesis inhibition mediated by $PA_{83}$ or 2-FHis $PA_{83}$ and $LF_N$-DTA (fusion of $LF_N$ and the catalytic domain of diphtheria toxin) into the cytosol of CHO-K1 cells. Plotted are averages of three or more experiments with error bars showing the standard deviation. Lines shown are data fitted to a standard $EC_{50}$ equation. Error bars represent the standard deviation. The insert shows an autoradiogram for a western blot of an SDS-PAGE of the cell lysate (right panel) of CHO-K1 cells incubated with either 5 μg WT $PA_{83}$ (lanes 1 and 3) or 2FHis $PA_{83}$ (lanes 2 and 4) as indicated and probed using an anti-PA antibody.

FIG. 3A shows urea denaturation of $PA_{83}$ (●) and 2-FHis $PA_{83}$ (■) measured using fluorescence (excitation 280 nm). Spectra represent the normalized emission intensity at 330 nm (ex. 280 nm). The data were fit using non-linear least squares analysis to a three-state N↔I↔U model. The inset in FIG. 3A shows the urea gradient gel electrophoresis of $PA_{83}$ and 2-His$PA_{83}$. Urea gradient gels were pre-run for 30 minutes at a constant current of 20 mA. Samples (25 μg in 75 μL) were applied to the top of the gels, and gels run for 16 hours at 20° C., 20 mA. FIG. 3B shows urea denaturation of WT $PA_{83}$ (●) and 2-FHis $PA_{83}$ (■) as measured in FIG. 3A, recording the emission wavelength maxima at each urea concentration. All spectra were recorded at 20° C., in 20 mM Bis-Tris/HEPES/cacodylic acid pH 8.0, and represent the average of 10 scans.

FIG. 4 shows the circular dichroism ("CD") spectra of WT $PA_{83}$ (FIG. 4A) and 2-FHis$PA_{83}$ (FIG. 4B) as a function of five pH values (5 ■, 6 ●, 7 □, 8 ○). All spectra were recorded at 20° C., and represent the average of five scans. FIG. 4 also shows fluorescence emission spectra of WT $PA_{83}$ (FIG. 4C) and 2-FHis$PA_{83}$ (FIG. 4D) as a function of five pH values (5 ■, 6 ●, 7 □, 8 ○). All spectra were recorded at 20° C. and represent the average of ten scans. Spectra values were recorded with an excitation wavelength of 280 nm, or with an excitation of 295 nm (inset).

FIG. 5A and FIG. 5B show the effect of pH on the fluorescence of WT and 2-FHis labeled protein that spans the range from pH 8 to 2, following either the peak maximum intensity (FIG. 5A) or the emission wavelength maximum (FIG. 5B). All measurements were carried out at 20° C. in a 10 mM BisTris/HEPES/cacedylic acid/citric acid buffer system. The data were fit using non-linear least squares analysis to the Henderson-Hasselbalch equation to derive an apparent pK ($pK_{app}$) for the pH transition to the full-length $PA_{83}$ (●) and 2-FHis$PA_{83}$ (■). The data were fit to the Henderson-Hasselbalch equation to give an apparent pK for the pH transition. FIG. 5C shows $^{19}$F-NMR spectra of 2-FHis $PA_{83}$ as a function of pH. The asterisk indicates resolvable resonances. The protein was at 50 μM, buffer was 10 mM each Tris-HCl/HEPES/acetate, pH 8, 7 and 5, 10% D2O. Note the chemical shift change from pH 8 to 7, with no further changes down to a pH of 5. Spectra were recorded at 500 MHz on a dedicated $^{19}$F-cryoprobe operating at 20 K (Washington University, St. Louis, Mo.). Spectra represent 1024 transients with 20 Hz line broadening.

FIG. 6A shows the conversion of $(PA_{63})_7$ and $(2\text{-FHisPA}_{63})_7$ from a prepore (pH 8) to a pore state using an SDS-PAGE assay. Each lane contains about 0.9 μM $PA_{63}$. Buffers (350 mM final) used were BisTris (pH 5 and 6) and HEPES (pH 7 and 8). FIG. 6B shows the kinetics of potassium release from DOPC liposomes as a result of PA pore insertion. Representative curves are shown for unlabeled (●) and 2-FHis-labeled (■) WT $(PA_{63})_7$ proteins. FIG. 6C shows translocation of $LF_N$ (residues 1-263 of LF) as a function of time during macroscopic conductance measurements taken using a planar phospholipids bilayer system. Representative planar lipid bilayer macroscopic conductance records are shown for WT and 2-FHis-labeled PA and records are normalized as fraction translocated.

FIG. 7 shows the gel filtration analysis of $PA_{83}$ and 2-FHis$PA_{83}$. Protein (1 mg/ml, 100 μL) was loaded onto a Superose 12 (GE-Healthcare) gel filtration column equilibrated in 20 mM Tris-HCl, 150 mM NaCl, pH 8. Calibration standards (High and Low molecular weight) were from GE-Healthcare. Each protein was run separately. The void volume (Vo) was determined using Blue Dextran 2000. Data were analyzed by calculating the gel-phase distribution coefficient (Kav) using the equation $Kav=(V_e-V_o)/(V_e—V_o)$, where $V_e$=elution volume, $V_o$=void volume, and $V_c$=geometric column volume (24 ml for a Superose 12); Stokes radii for each standard protein was listed in the Gel Filtration Calibration Kit product booklet (GE-Healthcare).

FIG. 8 shows gel filtration (FIG. 8A) and CD analysis (FIG. 8B) of $(PA_{63})_7$ (- - -) and $(2\text{-FHisPA}_{63})_7$ (-). Gel filtration was carried on a protein that was 10 μM $PA_{63}$, injecting 500 μL onto a Sephadex S-200 (GE-Healthcare) gel filtration column. The CD spectrum was also recorded with about 10 μM $(PA_{63})_7$ and $(2\text{-}FHisPA_{63})_7$ using a 0.1 mm pathlength cell at 20° C., in 20 mM Tris-HCl, pH 8.5, 0.4 M NaCl.

Figure 9:
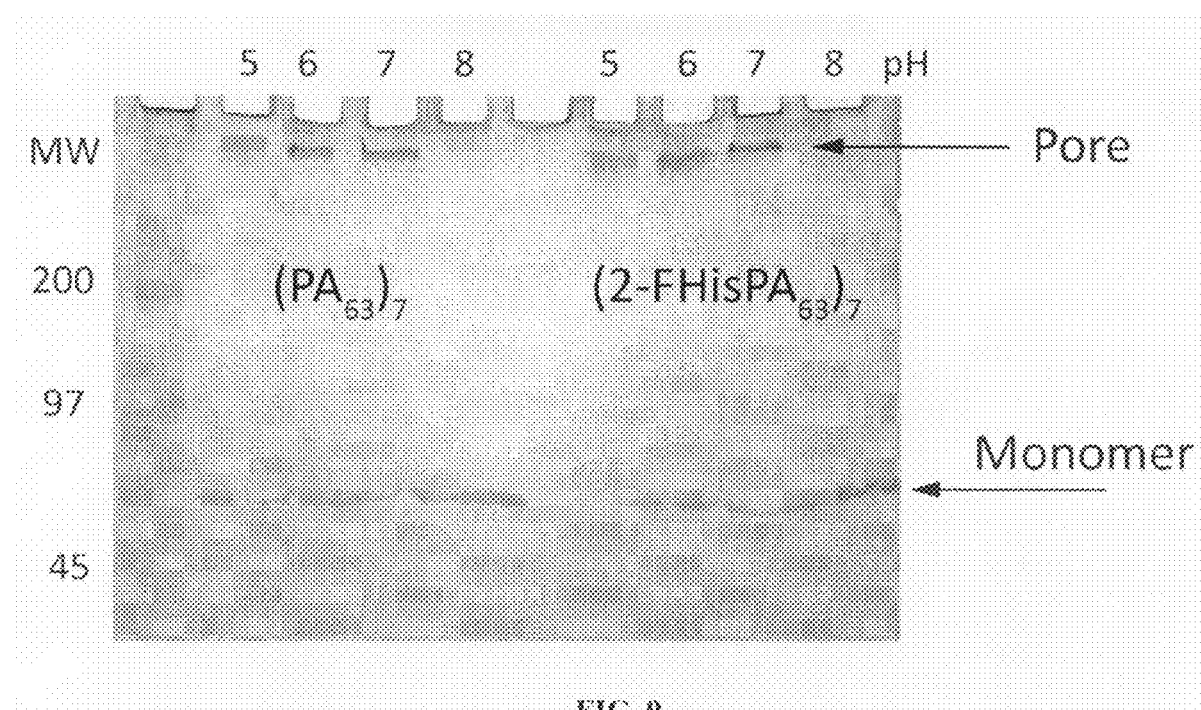

FIG. 9 shows the conversion of $(PA_{63})_7$ and $(2\text{-}FHisPA_{63})_7$ from a prepore (pH 8) to a pore state in the presence of ANTXR2. Each lane contains about 0.9 μM $PA_{63}$, and for the ANTXR2 experiments, 5 μM ANTRX2. Buffers (350 mM final) used were BisTris (pH 5 and 6) and HEPES (pH 7 and 8).

DETAILED DESCRIPTION OF PREFERRED EMBODIMENT

In the present invention, the effects of the biosynthetic incorporation of 2-FHis in place of histidine on the biochemical properties of the $PA_{83}$ and the heptameric $(PA_{63})_7$, the ability to form a pore, and the ability to function in planar lipid bilayers and in CHO-K1 cells was determined. There are a total of ten histidines in the wild-type $PA_{83}$ and four of the five histidine residues in domain 2 are part of the long β-barrel which comprises the transmembrane channel. The compound 2-FHis (shown below) is an isosteric analog of histidine with a side-chain pKa of about 1. These experiments are based upon a theory that protonation of histidine residues are important for the pre-pore to pore conversion of $(PA_{63})_7$.

In the present invention, it was shown that the modified PA proteins blocked translocation of a model cellular effector, $LF_N$-DTA, and also blocked cytotoxicity of the model cellular effector LFn-DTA, which upon entry into the cell cytosol through the pore blocks protein synthesis. However, the modified PA protein retains the ability to form a pore in the absence of the VWA domain of the cellular receptor, indicating that the structural features required for pore formation are retained. In addition, the structural properties of the protein as assessed by circular dichroism spectroscopy and stability to the chemical denaturant urea indicate that there is little perturbation to the structure of the protein as a result of 2-FHis incorporation.

Definitions

By an "effective amount" is meant herein an amount that is effective to elicit a desired response. For example, an effective amount of an immunogenic composition is an amount that is effective to elicit a detectable immune response. An effective dose can be determined empirically, according to conventional procedures, taking into account well-known factors such as the age, weight, and/or clinical condition of the subject, the method of and scheduling of administration, and the like.

The term "immune response" as used herein encompasses, for example, mechanisms by which a multi-cellular organism produces antibodies against an antigenic material that invades the cells of the organism or the extra-cellular fluid of the organism. The antibody so produced may belong to any of the immunological classes, such as immunoglobulin A, D, E, G, or M. Other types of responses, for example cellular immunity, such as the induction of cytotoxic T cells, are also included. Immune response to antigens is well studied and widely reported. A survey of immunology is given, e.g., in Roitt I., *Essential Immunology*, Blackwell Scientific Publications, London (1994). Methods in immunology are routine and conventional (see, e.g., *Currents Protocols in Immunology*; edited by John E. Coligan et al., John Wiley & Sons, Inc.).

An "immunogenic amount" is an amount of modified PA protein of the present invention sufficient to evoke an immune response in the subject to which the pharmaceutical composition or vaccine comprising the modified PA protein is administered.

"Protective antigen" or "PA" means a polypeptide that is at least 80%, preferably at least 90%, more preferably at least 95%, still more preferably at least 97%, or most preferably at least 99% identical to GenBank AF306778 (SEQ ID NO. 1), which is incorporated by reference. See also FIG. 1C. The polypeptide may be encoded by the PA gene that was reported by Vodkin et al., *Cloning of the protective antigen gene of Bacillus anthracis*, Cell 34 693-697 (1983). The polypeptide can be identical to wild-type PA characterized by Miller et al., *Anthrax Protective Antigen. Prepore-to Pore Conversion*, Biochemistry 38(32) 10432-10441 (1999), UniProt:Swiss-Prot: P13423, which is incorporated by reference, or any naturally-occurring PA polypeptide from a strain of *Bacillus anthracis*. The PA polypeptide may be cloned and expressed in a heterologous host such as *Escherichia coli* or *Bacillus subtilis*. The host used in the present study, the *E. coli* strain UTH780, is a strain that is auxotrophic for histidine. It is understood that homologs and analogs have the characteristics of the anthrax PA described herein and may be used in the methods of the invention. The term also includes any recombinant *B. anthracis* PA, or other modified form (variant).

"$PA_{63}$" means the carboxy-terminal portion of the PA that results from proteolytic cleavage of a 20 kDa N-terminal segment from the PA polypeptide. Wild-type $PA_{63}$ forms a heptameric prepore and binds the two alternative A moieties, EF and LF. The entire complex is trafficked to an acidified endosome, where $PA_{63}$ inserts into the membrane, forms a transmembrane pore, and translocates EF and LF into the host cell cytoplasm.

The term "protection" or "protective immunity" refers herein to the ability of the serum antibodies and cellular response induced during immunization to protect (partially or totally) against anthrax. Thus, a subject immunized by the pharmaceutical compositions or vaccines of the invention will experience limited growth and spread of the anthrax organism compared to a control.

"Transmembrane pore" means a transmembrane aqueous channel. For example, the transmembrane pore can be a beta-barrel channel formed by alternating hydrophilic and hydrophobic residues of $PA_{63}$ such that the hydrophobic residues form an exterior membrane-contiguous surface of the barrel, and the hydrophilic residues face an aqueous lumen of a pore that spans across the host cell membrane.

As used herein, the term "treating" refers to a process by which the symptoms of a anthrax infection are alleviated or completely eliminated. As used herein, the term "preventing" refers to a process by which an anthrax infection is obstructed or delayed.

As used herein, "percent identity" between amino acid or nucleic acid sequences is synonymous with "percent homology," which can be determined using the algorithm of Karlin and Altschul (Proc. Natl. Acad. Sci. USA 87 2264-2268

(1990)), modified by Karlin and Altschul (Proc. Natl. Acad. Sci. USA 90 5873-5877, (1993)). Such an algorithm is incorporated into the NBLAST and XBLAST programs of Altschul et al., *Basic Local Alignment Search Tool*, J. Mol. Biol. 215 403-410, (1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO. 1). To obtain gapped alignments for comparison purposes, Gapped BLAST is utilized as described in Altschul et al., *Gapped BLAST and PSI-BLAST: A new generation of protein database search programs*, Nucleic Acids Res. 25 3389-3402 (1997). When utilizing BLAST and Gapped BLAST programs, the default parameters of the respective programs (e.g., XBLAST and NBLAST) are used which are available from the National Institutes of Health. A variant can also include, e.g., an internal deletion or insertion, a conservative or non-conservative substitution, or a combination of these variations from the sequence presented.

As used herein, the "subject" is includes an individual suffering from or at risk of developing to *Bacillus anthracis* infection. The subject is preferably a mammal such as a human, primate, mouse, rat, dog, cat, cow, horse, pig, ox, goat, antelope, buffalo, or rabbit.

A subject suffering from or at risk of developing *Bacillus anthracis* may be identified by methods known in the art, e.g., by isolating *B. anthracis* from the blood, skin lesions, or respiratory secretions or by measuring specific antibodies in the blood. Symptoms of *B. anthracis* infection include fever (temperature greater than 100° F.), chills or night sweats, flu-like symptoms, cough, usually a non-productive cough, chest discomfort, shortness of breath, fatigue, muscle aches, sore throat, followed by difficulty swallowing, enlarged lymph nodes, headache, nausea, loss of appetite, abdominal distress, vomiting, or diarrhea or in the case of cutaneous contraction, a sore, especially on the face, arms or hands, that starts as a raised bump and develops into a painless ulcer with a black area in the center.

Pharmaceutical Compositions

The invention relates to modified PA (e.g., 2-FHis PA), and/or compositions containing the modified PA protein, which are useful for eliciting an immunogenic response in mammals, in particular humans, including responses which provide protection against, or reduce the severity of, infections caused by *B. anthracis*. The invention also relates to methods of using such modified PA, and/or compositions thereof, to induce serum antibodies against PA. The modified PA protein, and/or compositions thereof, are useful as vaccines to induce serum antibodies which are useful to prevent, treat, or reduce the severity of infections caused by *B. anthracis*, such as inhalation anthrax and/or cutaneous anthrax. The PAs of this invention are expected to induce a strong protective IgG antibody response in mammals, including humans.

The invention also relates to a method for the prevention or treatment of *B. anthracis* infection in a mammal, by administration of compositions comprising the modified PA proteins of the invention.

The invention also relates to the use of the modified PA as an anti-toxin for the treatment of a concurrent infection, through association of the modified PA with the secreted WT PA, which neutralizes the functional capability of translocation and pore formation required for toxicity. The modified PA of the present invention may associate with secreted EF and LF, and host cell receptors, but is non-functional in carrying out pore formation and/or translocation.

The invention also relates to kits for vaccinating mammals for the treatment or prevention of *B. anthracis* infection in a mammal comprising the modified PA proteins of the invention.

The present invention also encompasses methods of using mixtures of one or more of the modified PA proteins of the invention, either in a single composition or in multiple compositions containing other immunogens, to form a multivalent vaccine for broad coverage against either *B. anthracis* itself or a combination of *B. anthracis* and one or more other pathogens, which may also be administered concurrently with other vaccines, such as the DTP vaccine.

Preferred immunogenic compositions according to the invention are formulations comprising at least about 2 µg per dose of the modified PA protein (e.g., 2-FHis PA), e.g., an immunogenic composition according to this invention may provide 1 µg, 2 µg, 5 µg, 25 µg, 50 µg, 100 µg, 250 µg, 500 µg, 750 µg, 1000 µg, or more of modified PA protein per dose. See Jones et al., *Efficacy of the UK human anthrax vaccine in guinea pigs against aerosolised spores of Bacillus anthracis*, Salisbury Medical Bulletin, special supplement #87, 123-124 (1995). Preferably, a desired anti-PA antibody titer will be obtained in the subject.

Anti-PA titer, measured as the reciprocal of the dilution of serum at which no PA-reactive antibody is detected, is a common measure of the effectiveness of anthrax vaccines. See, e.g., Pittman et al., *Anthrax vaccine: increasing intervals between the first two doses enhances antibody response in humans*, Vaccine, 19 213-216 (2000). The method of immunization described herein involves administering an initial dose of a modified PA protein composition, optionally followed by repeated administrations, or boosts, over time. The interval between repeated administrations of the immunogenic composition may vary, and judicious spacing of the doses can increase the immune response, as measured by anti-PA titer. Any spacing of doses may be employed that achieves the desired immune response. Administration of immunogenic modified PA protein compositions of the invention according to the methods of the invention preferably results in anti-PA antibody titers of greater than 1000, more preferably greater than 5000, more preferably greater than 10,000, more preferably greater than 50,000, more preferably greater than 100,000 or higher.

Those skilled in the art will appreciate that depending on the intended mode of administration, the modified PA protein of the present invention can be in various pharmaceutical compositions. The compositions will comprise the modified PA protein in a therapeutically effective amount in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the immunogen and/or antibody or other composition without causing any undesirable biological effects or interacting in a deleterious manner with any of the other components of the pharmaceutical composition in which it is contained.

The immunogenic compositions of the present invention may be formulated by dispersing modified PA protein in the desired amount in any pharmaceutical carrier suitable for use in vaccines. Typical doses of anthrax vaccine are 0.5 mL in volume, but any volume suitable to deliver the desired amount of modified PA protein can be used, for example, 0.05 mL to 1.0 mL or more. Accordingly, a typical immunogenic composition according to the invention may be a solution of modified PA protein dispersed in a pharmaceutical carrier providing 50 to 1000 or more µg modified PA protein per 0.5 mL of solution. Any pharmaceutical carrier suitable for administration to mammals which does not interfere with the immunogenicity of the modified PA protein may be employed. Preferred carriers are sterile "water for injection," saline, and Ringer's Solution.

In view of the discoveries herein, a preferred embodiment of the present invention is a vaccination kit comprising one or more containers of a pharmaceutically effective dose of the modified PA protein in a formulation for injection (intravenous, intramuscular, subcutaneous or intraperitoneal) together with instructions for following the vaccination method of the present invention. Advantageously, the kit could contain, e.g., three or four sterile ampules, each ampule containing one dose of 1 to 1000 or more µg of modified PA protein (and optionally other active agents), such ampules representing a vaccination regimen of an initial immunization plus one, two, or three booster injections.

The modified PA protein of the invention can be co-administered with one or more other therapeutic or immunostimulatory agents. Further, the modified PA protein can be administered before, after or concurrently with the agent or can be co-administered with other known therapies including anthrax vaccines, antibodies against LF, EF, PA, and $B.$ $anthracis$ antibiotics, e.g., amoxicillin, penicillin G procaine, ciprofloxacin, doxycycline, chloramphenicol, clindamycin, tetracycline, rifampin, and vancomycin.

One preferred optional additional component of the immunogenic compositions according to the present invention is $LF_N$, which may be any N-terminal fragment of the $B.$ $anthracis$ LF capable of eliciting anti-LF antibodies and incapable of forming the lethal binary toxin. LF has also been cloned and sequenced. See, Robertson et al., $Molecular$ $cloning$ $and$ $expression$ $in$ $Escherichia$ $coli$ $of$ $the$ $lethal$ $factor$ $gene$ $of$ $Bacillus$ $anthracis$, Gene 44 71-78 (1986); and Bragg et al., $Nucleotide$ $sequence$ $and$ $analysis$ $of$ $the$ $lethal$ $factor$ $gene$ $(lef)$ $from$ $Bacillus$ $anthracis$, Gene 81(1) 45-54 (1989). Preferred $LF_N$ polypeptides comprise the N-terminal portion of LF necessary to bind to PA but does not include the catalytic domain of LF. Most preferably, $LF_N$ consists essentially of amino acids 1-254 of native LF. The 254-amino acid $LF_N$ contains the PA-binding domain of LF but not the catalytic domain necessary to form anthrax toxin. Moreover, $LF_N$ that includes the PA-binding domain will be useful for introducing an $LF_N$ fusion partner, e.g., a subunit vaccine, into target cells, according to methods described in WO 94/18332, WO 97/23236, and WO 98/11914, which are incorporated by reference.

Compositions of the invention may be administered to any subject including humans in which it is desired to elicit an immune response against $B.$ $anthracis$. In addition to humans, the compositions of the present invention may advantageously be administered, for example, to horses, cattle, oxen, goats, sheep, dogs, cats, antelope, buffalo, rabbits, pigs, and the like.

Compositions of the invention may be administered in any manner used for administration of vaccines. Preferably, the compositions according to the invention will be administered subcutaneously, intradermally, intramuscularly, intravenously, or orally. The most preferred means of administration is via subcutaneous or intramuscular injection.

The invention will be more fully understood upon consideration of the following non-limiting examples.

Reagents, Plasmids, Strains

In the following, examples, all buffers for purification and analysis were either from Sigma or Fisher Scientific, and were reagent grade. Synthesis of 2-FHis was performed as described previously in Kirk et al., $Photochemistry$ $of$ $Diazonium$ $Salts$, J. Amer. Chem. Soc. 38, 4619-4624 (1972); Kirk et al., $Photochemistry$ $of$ $Diazonium$ $Salts$, J. Amer Chem. Soc. 95, 8389-8392 (1973); and Yeh et al., $^{19}F$ $and$ $^{1}H$ $nuclear$ $magnetic$ $resonance$ $studies$ $of$ $ring$-$fluorinated$ $imidazoles$ $and$ $histidines$, J. Chem. Soc. Perkin Trans. 2, 928-934 (1975). The histidine auxotroph UTH780 was obtained from the $E.$ $coli$ Genetic Stock Center at Yale University (New Haven, Conn.). The gene encoding $PA_{83}$ in pET22b(+) (see Wigelsworth et al., $Binding$ $Stoichiometry$ $and$ $Kinetics$ $of$ $the$ $Interaction$ $of$ $a$ $Human$ $Anthrax$ $Toxin$ $Receptor$, $CMG2$, $with$ $Protective$ $Antigen$, J. Biol. Chem. 279, 23349-23356 (2004)), which is under a T7 promoter, was moved to the plasmid pQE80 (Qiagen) by first removing the EcoR1 site in pET22b-$PA_{83}$ using the Quikchange mutagenesis kit (Stratagene). The following with primers (Sigma Genosys) were used:

```
                                         (SEQ ID NO.2)
5'-GCAGGATTTAGTAATTCGAACTCAAGTACGGTCGC-3'

(SEQ ID NO.3)
5'-GCGACCGTACTTGAGTTCGAATTACTAAATCCTGC-3'
```

This directed a silent change from G<u>AA</u>TTC (AAT=Asn) to G<u>AA</u>CTC (AAC=Asn), and then using PCR to clone $PA_{83}$ (including the phoA signal sequence from pET22b(+)) as an EcoR1/KpnI fragment into pQE80. The following primers were used:

```
Forward primer:
                                         (SEQ ID NO.4)
5'CCCGAATTCATTAAAGAGGAGAAATTAACTATGAAATACCTGCTGCCG

ACC-3';

Reverse primer:
                                         (SEQ ID NO.5)
5'GGGGGTACCTCAGCTAATTATCCTATCTCATAG-3'.
```

Cloning of the VWA domain of ANTXR2 was carried out using a human cDNA corresponding to the full-length ANTXR2 obtained from Origene Technologies (Rockville, Md.). PCR was used to clone the von-Willebrand factor A domain of ANTXR2 (residues 38-218) into the expression plasmid pGEX-4T1, affording the new plasmid pGEX-4T1-ANTXR2 (residues 38-218). The following primers were used;

```
Forward:
                                         (SEQ ID NO.6)
5'-CCGCGTCCATCCTGCAGAAGAGCCTTTGATCTC-3';

Reverse:
                                         (SEQ ID NO.7)
5'-GGGGATGCGGCCCTCAGTCAACATGACTGAGCTAGTATAG-3'.
```

Sequences were verified by the Protein and Nucleic Acid Chemistry Laboratory (PNACL) at Washington University (St. Louis, Mo.).

Example 1

Labeling with 2-FHis

UTH780 cells were transformed with plasmids encoding PA and were grown in the presence of 100 μg/ml of ampicillin. The medium for growth was a modified version of the ECPM1 media in Wigelsworth et al., *Binding Stoichiometry and Kinetics of the Interaction of a Human Anthrax Toxin Receptor, CMG2, with Protective Antigen*, J. Biol. Chem. 279 23349-23356 (2004) but with defined amino acids and glucose (0.5%) instead of NZ amine, yeast extract and glycerol. See Frieden et al., *The preparation of 19F-labeled proteins for NMR studies*, Methods Enzymol. 380, 400-415 (2004). The cells were grown to an $A_{600}$ of 3 in Fernbach shaker flasks at 32° C. The cells were then washed twice with 0.9% NaCl, and then the same media containing 0.2 mM 2-FHis in place of histidine (0.2 mM) was added to the cells and resuspended. The cells were then incubated for 10-15 minutes with shaking prior to the addition of isopropyl-β-d-thiogalactopyranoside ("IPTG") to 1 mM. After growth at 26° C. for three hours, the cells were harvested in a centrifuge equipped with a swinging bucket rotor (3000×g) for 10 minutes, and then placed on ice for purification.

For purification of the $PA_{83}$ proteins, the cells were resuspended in 500 ml of 20 mM Tris-HCl, pH 8, 20% sucrose, and 1 mM EDTA, and incubated for 15 minutes at room temperature with gentle stirring. The cells were centrifuged for 15 minutes at 4° C. (8000×g), the supernatant removed, and cells resuspended in ice-cold 5 mM $MgSO_4$, and stirred for 15 minutes at 4° C. After the addition of 1 M Tris-HCl pH 8.0 to a final concentration of 20 mM, the cells were centrifuged again at 4° C. (8000×g). The supernatant was removed and applied to a Hi-Trap Q anion exchange column (GE-HealthCare) equilibrated in 20 mM Tris-HCl, pH 8.0 (4° C.) and eluted with a NaCl gradient on an AktaPrime LC (GE-Healthcare). Fractions were pooled, concentrated using an Amicon Ultra-15 10 kD cutoff centrifugal filter (Millipore), and then applied to a Sephadex S-200 gel filtration column (GE-HealthCare) equilibrated in 20 mM Tris-HCl, 150 mM NaCl, pH 8.0 (4° C.). Fractions containing pure protein were identified using SDS-PAGE, pooled and concentrated. Protein concentration was determined using a calculated extinction coefficient of 80,220 $M^{-1}$ $cm^{-1}$ (see Pace et al., *How to measure and predict the molar absorption coefficient of a protein*, Protein Sci. 11, 2411-2423 (1995)).

For FT-MS measurements, protein samples were desalted on a 1.5 cm×1 mm inner diameter column hand-packed with Zorbax SB-C8, 5 μm (Agilent Technologies, Wilmington, Del.). A linear gradient was developed by the Ultra-Plus II (Micro-Tech Scientific, Vista, Calif.) using aqueous 0.1% TFA as mobile phase A, and isopropanol/acetonitrile/water/TFA 80/10/9.9/0.1 (v/v/v/v) as mobile phase B. Proteins were directly eluted into the ESI source of a Finnigan LTQ-FT hybrid linear quadrupole ion trap Fourier transform ion cyclotron resonance (FT-ICR) mass spectrometer (Thermo-Electron, Bremen, Germany). Calibration of the instrument was performed biweekly with caffeine (Sigma), MRFA (tetrapeptide, Thermo-Electron), Ultramark 1621 (Perfluoroalkylphosphazine, Lancaster) in the mass range of 195-2000 u. Spectra were acquired in positive mode over the m/z mass range 500-2000 with the FT-ICR operated at resolution (50,000) using automated gain control (AGC) value of $5\times10^5$ or a maximum ion accumulation time of 3000 ms. The ESI source was operated with spray voltage of 4 kV, a tube lens offset of 115 V and a capillary temperature of 200° C. All other source parameters were optimized for maximum sensitivity of most abundant multiply charged ions of Lysozyme. Spectra were smoothed and deconvoluted using ProMass for Xcalibur, version 2.5 SR-1. Importantly, the $PA_{83}$ was found to be more than 95% labeled with 2-FHis as evidenced by mass spectrometry (FIG. 1).

Example 2

Equilibrium Stability of 2-FHis and WT $PA_{83}$

In this example, urea gradient gel electrophoresis was used along with fluorescence emission as a function of urea concentration to determine the relative stability of 2-FHis$PA_{83}$ to that of the WT protein.

Fluorescence Spectra

Figure 3A:
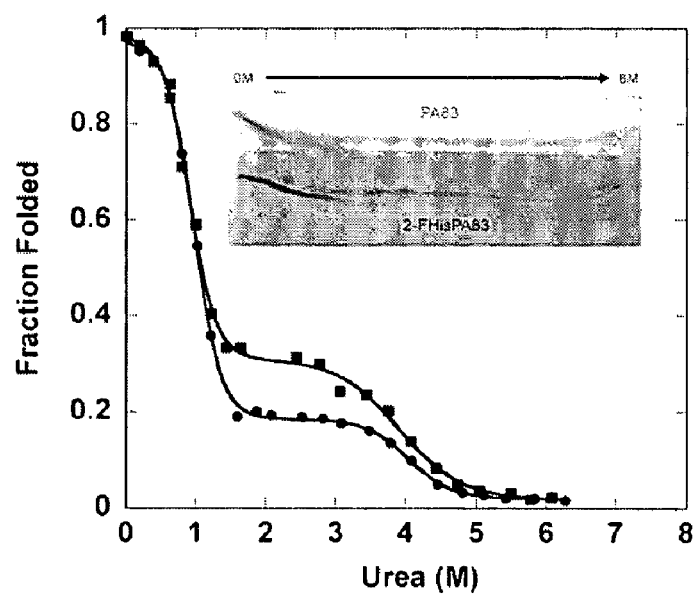
Figure 3B:
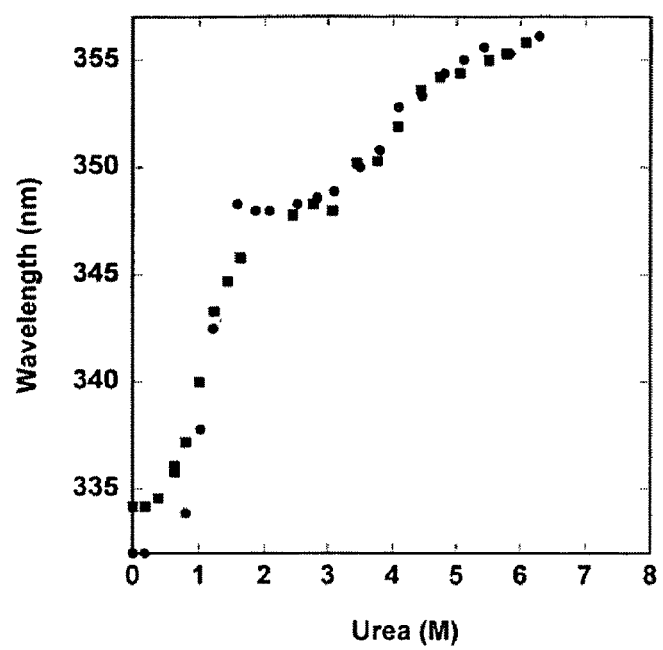
Figure 4A:
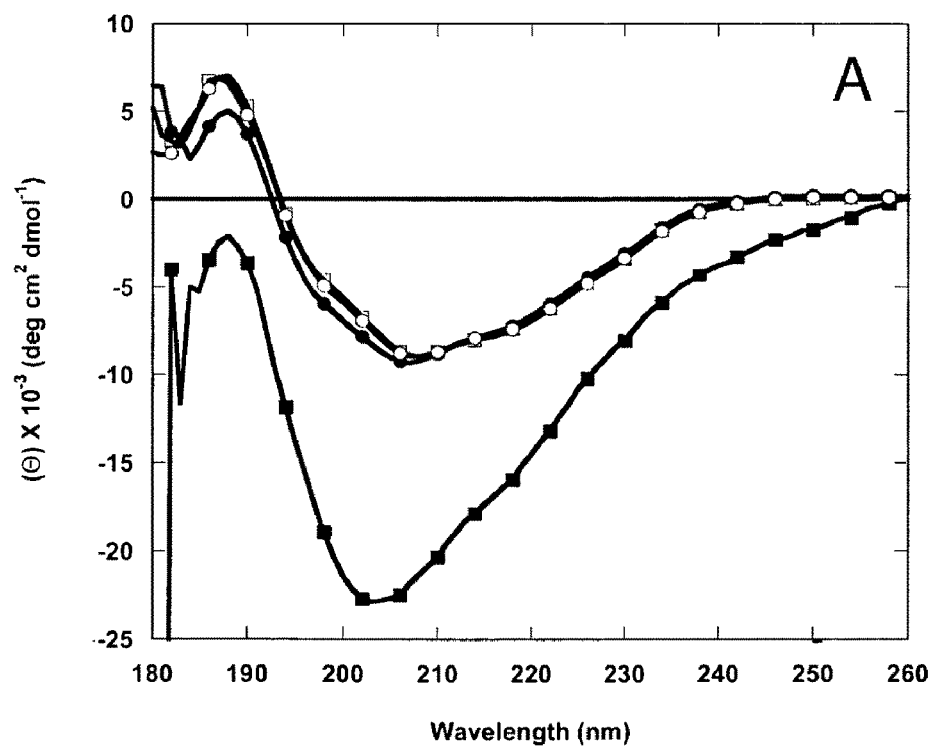
Figure 4B:
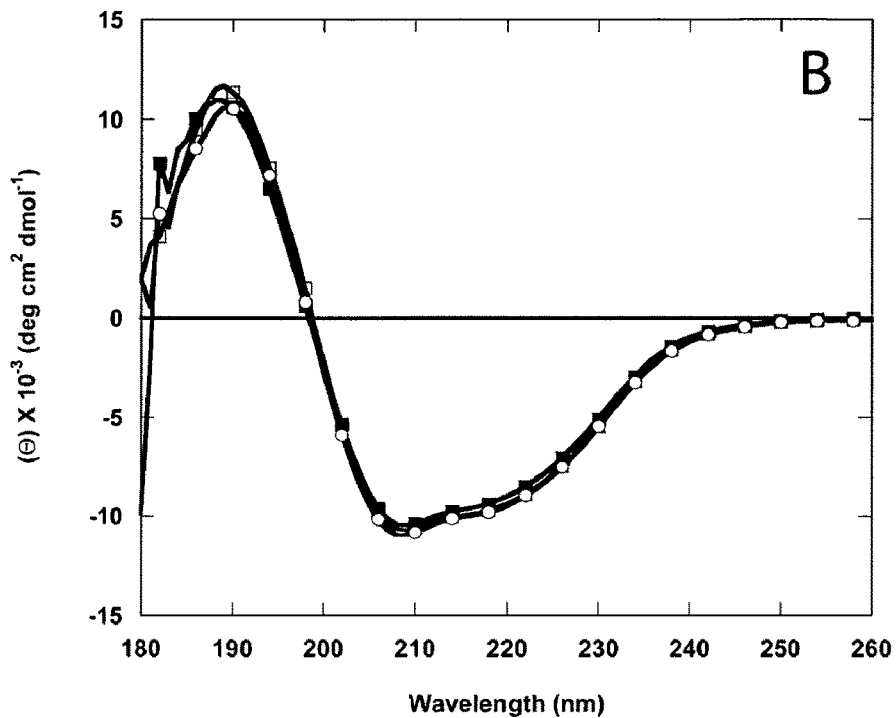
Figure 4C:
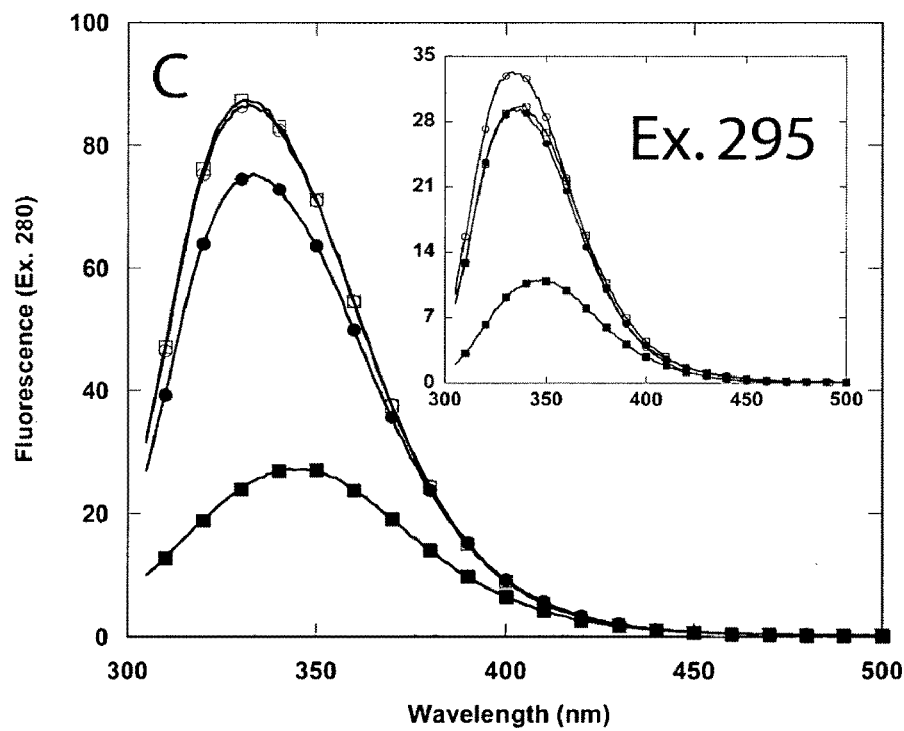
Figure 4D:
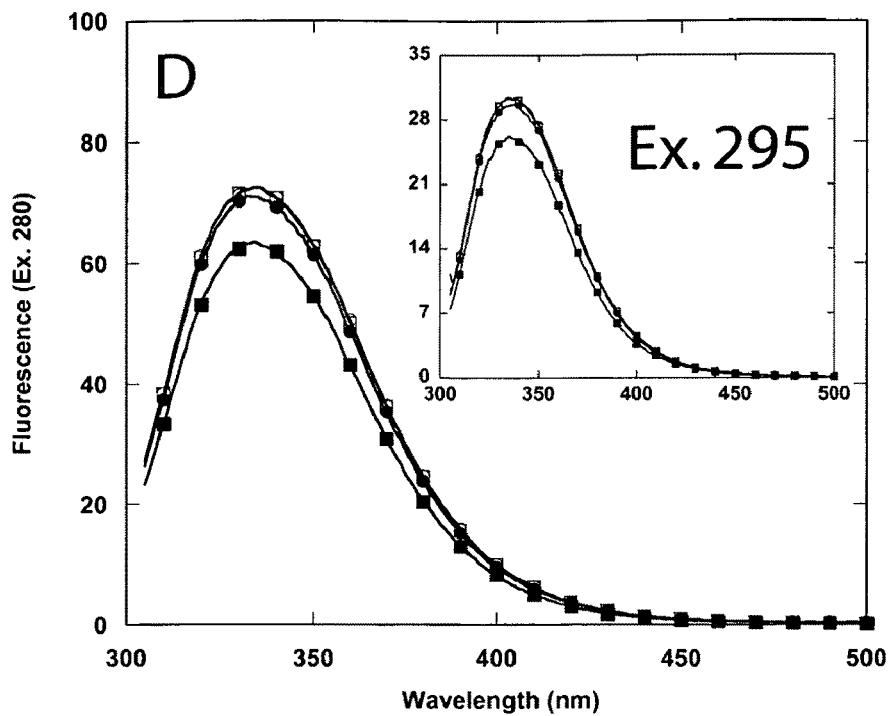

Fluorescence spectra of $PA_{83}$ and 2-FHis$PA_{83}$ were acquired on a Cary Eclipse spectrofluorometer. All experiments were done at 20° C., and the concentrations were kept at an $A_{280}$ of 0.01 (about 0.1 μM) in 10 mM HEPES (sodium salt)/Bis-Tris/cacodylic acid pH 8.0 containing urea. Urea concentrations were determined by measuring the refractive index (see Pace et al., *Protein Structure: A Practical Approach, 2nd ed.* (Ed.: T. E. Creighton) Oxford University Press, Oxford, U.K (1997)). Spectra represent the mean of ten scans. Emission spectra were recorded with an excitation wavelength of 280 or 295 nm (10 nm slit width) with 5 nm slit width for the emission scan (305-600 nm). Urea denaturation data were fit to a three-state stability equation (Native(N)↔Intermediate(I)↔Unfolded(U)) (29-30), where the equilibrium constants $K_{N\rightarrow I}$ and $K_{I\rightarrow U}$ are:

$$K_{N\rightarrow I}=\exp(-\Delta G^o_{N\rightarrow I}-m^*[D])/RT \quad (1)$$

$$K_{I\rightarrow U}=\exp(-\Delta G^o_{I\rightarrow U}-m^*[D])/RT \quad (2)$$

wherein D is the denaturant concentration, R is the universal gas constant, and T is temperature in Kelvin.

Assuming that only N, I, and U are populated during unfolding, then the fractional population of each species in solution during the titration can be represented by:

$$Fl_{(obs)}=*Fl_N f_N+*fIFl_I fI+Fl_U f_U \quad (3)$$

$$Fl_{(obs)}=(Fl_N-*Fl_I K_{N\rightarrow I}+*Fl_U K_{N\rightarrow I}*K_{I\rightarrow U})/(1+K_{N\rightarrow I}+K_{N\rightarrow I}*K_{I\rightarrow U}) \quad (4)$$

wherein $f_N$, $f_I$ and $f_U$ are the fractions of N, I, and U, respectively. The pre- and post-transition baselines are assumed to be flat. The data were normalized using the equation y=Fl(obs)−$Fl_U$/$Fl_N$−$Fl_U$. The data were fit by non-linear least squares analysis according to equation 4 using Kaleidagraph software.

Urea Gradient Gel Electrophoresis

Urea gradient gels were prepared according to the protocol of Goldenberg, *Protein Structure: A Practical Approach, 2nd ed.* (Ed.: T. E. Creighton) Oxford University Press, Oxford, U.K (1997). Urea gradient gels were pre-run for 30 minutes at a constant current of 20 mA. Samples (25 μg in 75 μL) were applied to the top of the gels, and gels run for 16 hours at 20° C., 20 mA.

The data are shown in FIG. 3. As shown in FIG. 3A, there are two separate transitions in the fluorescence data, the first from about 0 to about 2 M urea, and another from about 2 to about 6 M urea, indicating the presence of a stable intermediate in the unfolding process (see Yan et al., *Characterization of Dominant-Negative Forms of Anthrax Protective Antigen*, Mol. Medicine. 9 46-51 (2003); and Gupta et al., *Conformational fluctuations in anthrax protective antigen: a possible role of calcium in the folding pathway of the protein*, FEBS Letters 554 505-510 (2003)).

In this example, the fluorescent experiments were followed by measuring the emission wavelength maximum (FIG. 3B).

The results mirror-image the normalized total emission intensity data (FIG. 3A), and indicate that the spectroscopic properties of the two transitions are unique.

The unfolding data by fluorescence were fit using a three-state model, and the thermodynamic parameters are summarized in Table 1. Both the WT and 2-FHis labeled proteins exhibit similar denaturation profiles, indicating that the global stability of the protein (to urea) was not affected by incorporation of 2-FHis.

water bath. Samples of $PA_{83}$ or 2-FHisPA$_{83}$ (about 10-17 μM) in 10 mM HEPES (sodium salt)/Bis-Tris/cacodylic acid at the requisite pH, were placed in a water-cooled 0.1 mm circular CD cell, and spectra recorded at 20° C. from 260 to 180 nm at a scan rate of 20 nm/min, and a response time of 4 seconds. Spectra are the average of five scans. The spectra were recorded after allowing the samples to equilibrate at the respective pH for least 24 hours. Some (less than 10%) visible precipitation of both the WT PA$_{83}$ and 2-FHisPA$_{83}$ labeled

TABLE 1

Thermodynamic Parameters for the Equilibrium Unfolding of PA$_{83}$ and 2-FHisPA$_{83}$

| | pKapp[c] | [b]$\Delta G°_{N \to I}$ (kcal/mol) | $\Delta G°_{I \to U}$ (kcal/mol) | $m_{N \to I}$ (kcal/mol) | $m_{I \to U}$ (kcal/mol) | [a]$[D_{1/2}]_{N \to I}$ (M) | $[D_{1/2}]_{I \to U}$ (M) |
|---|---|---|---|---|---|---|---|
| PA$_{83}$ | 5.9 +/− 0.3 | 12.5 ± 1.0 | 33.2 ± 2.0 | 12.8 ± 0.6 | 8.1 ± 1.6 | 0.98 ± 0.01 | 4.10 ± 0.06 |
| 2-FHis PA$_{83}$ | 3.6 +/− 0.4 | 11.7 ± 1.0 | 21.8 ± 1.0 | 12.9 ± 1.0 | 5.5 ± 1.0 | 0.91 ± 0.02 | 3.96 ± 0.09 |

[a]$D_{1/2}$ = midpoint in the urea denaturation curve.
[b]= errors were determined from the fits to a three (b) (29) or two-state(c) model (28) using non-linear least squares in Kaleidagraph.
[c]errors were determined by a best-fit to the Henderson-Hasselbalch equation using non-linear least squares analysis in Kaleidagraph.

Example 3

Effect of 2-FHis on the Stability of PA$_{83}$ to pH

To assess the effect of pH on the structure and stability of PA$_{83}$ and 2-FHisPA$_{83}$, this example compared the equilibrium stability as a function of pH by fluorescence and circular dichroism ("CD") spectroscopy. See Barrick et al., *Molecular Mechanisms of Acid Denaturation: The Role of Histidine Residues in the Partial Unfolding of Apomyoglobin*, J. Mol. Biol. 237, 588-601 (1994).

For the pH studies of PA$_{83}$ and the 2-FHis labeled counterpart, measurements by fluorescence (FIG. 4 and FIG. 5) were carried out in a similar manner at 0.38 mM in a 10 mM Bis-Tris/HEPES/cacodylic acid/citric acid buffer system. Consistent with the observed transitions by urea that allowed one to distinguish the wavelengths for the N, I, and U states, the pH transitions were fit using non-linear least squares to the Henderson-Hasselbalch equation, assuming a two-state protonation equilibrium:

$$Fl_{(obs)} = (Fl_N + Fl_I 10^{pH-pKapp})/(1+10^{pH-pKapp}) \quad (5)$$

wherein pK$_{app}$ represents an apparent pKa encompassing all classes of titratable sites.

Circular dichroism spectra were acquired on a Jasco J-810 spectropolarimeter equipped with a temperature controlled water bath.

proteins occurred at pH 5, and so these samples were centrifuged for 10 minutes on high speed in a microfuge, and the supernatant was used for both concentration determination and generation of the CD spectrum. Data are normalized to the mean residue ellipticity based on a value of 734 peptide bonds. Analyses of the CD spectra were done using the CDNN program available from Martin Luther University of Halle-Wittenberg.

FIG. 4 shows the CD and fluorescence emission spectra (excitation at 280 nm and 295 nm) of the WT PA$_{83}$ (FIG. 4A and FIG. 4C) and 2-FHisPA$_{83}$ (FIG. 4B and FIG. 4D) labeled proteins as a function of pH. Very little change occurs in the fluorescence and CD spectra from 8 to 6. At about pH 5, the peak maximum of the WT protein is red-shifted to about 345 nm and the CD spectrum exhibits a single minimum at 203 nm, indicating partial unfolding. Very little change occurs in the 2-FHis labeled protein with decreasing pH, which suggests that 2-FHis incorporation prevents pH-dependent unfolding (at least down to pH 4, see FIG. 5). The CD spectra of the WT and 2-FHis labeled proteins differ slightly in their secondary structure. The maxima and minima values are listed in Table 2, along with the calculated percent secondary structure content as determined using the program CDNN. The spectra indicate that the helical content increases for the 2-FHis labeled protein with a corresponding decrease in β-sheet content.

TABLE 2

Circular dichroism analysis of PA$_{83}$ and 2-FHisPA$_{83}$

| | %-helix | %-β-sheet (parallel) | % β-sheet (antiparallel) | %-β-turn | %-random | Max (nm) | Min (nm) | Min (nm) | Min (nm) |
|---|---|---|---|---|---|---|---|---|---|
| WT | 13.3 | 3.0 | 31.9 | 21.9 | 33.6 | 187 | 203 | 207 | 219 |
| 2FHis | 19.8 | 4.6 | 20.5 | 20.6 | 31.7 | 189 | — | 208.3 | 220.7 |
| Actual[a] | 13.8 | [b]ND | 30 | ND | ND | | | | |

[a]PDB: 1ACC (see Ref. 35).
[b]ND = not determined

Figure 5A:
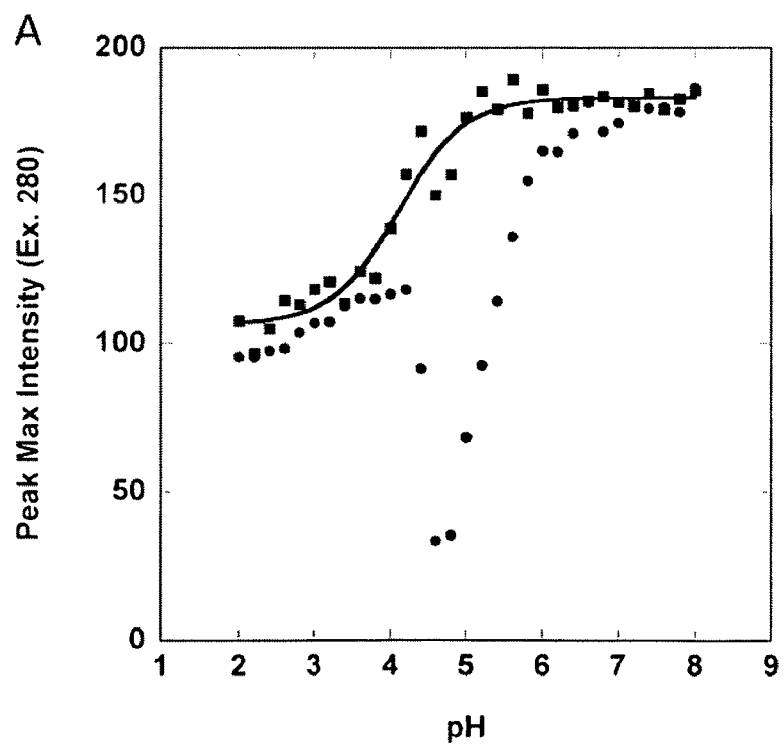
Figure 5B:
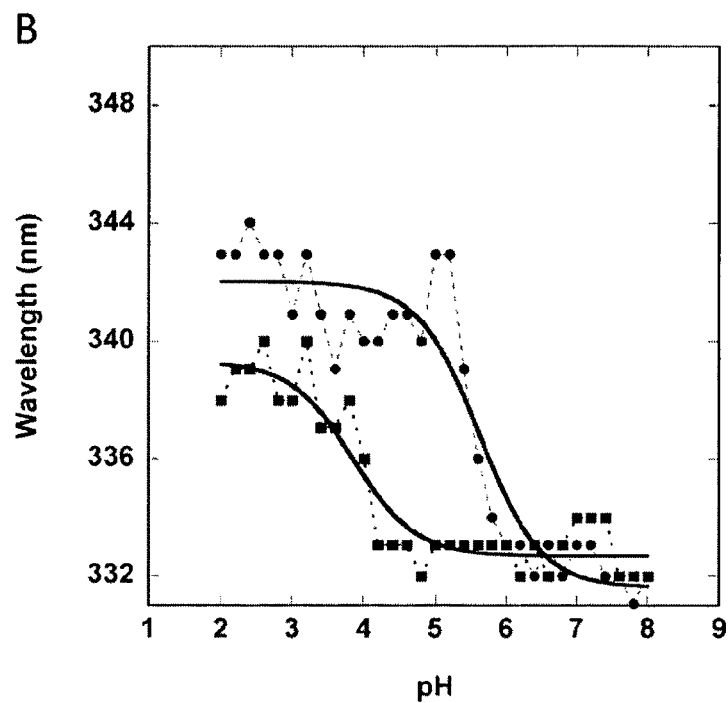

FIG. 5A and FIG. 5B show the effect of pH on the fluorescence of WT and 2-FHis labeled proteins that spans the range from pH 8 to 2, following either the peak maximum intensity (FIG. 5A) or the emission wavelength maximum (FIG. 5B). The data were fit using non-linear least analysis to the Henderson-Hasselbalch equation to derive apparent pKa (pKapp) values and are summarized in Table 1. While both proteins are stable down to about pH 6, the WT protein undergoes changes in both the wavelength and total intensity down to about pH 4.5, with wavelength values comparable to the I state observed in the urea denaturation profile. The lower intensity values in the range of 6 to 4.5 (FIG. 5A) may be due to aggregation even at these low (0.4 µM) concentrations, since visible precipitation was observed at pH 5 in the CD experiments, which dropped the soluble concentration from 17 µM to 10 µM. The aggregation was less for the 2-FHis labeled protein, which may account for the intensity change observed within the range of pH 5 to 4 (FIG. 5A). However, no change in the wavelength maximum occurred down to pH 4 (pKapp=3.6), again showing that the 2-FHis labeled protein is significantly more stable to pH (about 1-2 units) than the WT protein.

Example 4

$^{19}$F-NMR Studies on PA$_{83}$

In this example, fluorine NMR studies were carried out on a Varian 500 MHz NMR equipped with a cryoprobe operating at 20 K. Protein was at 50 µM, and the buffer was 10 mM each of Tris-HCl/HEPES/sodium acetate, pH 8, 7, and 5, 10% D$_2$O. Spectra in 6 M urea were carried out in 10 mM Bis-Tris/HEPES/cacodylic acid, pH 8, wherein Bis-Tris is bis(2-hydroxyethyl)amino-tris(hydroxymethyl)methane and HEPES is N-(2-hydroxyethyl)piperazine-N'-(2-ethane sulfonic acid). Spectra represent 1024 transients with 20 Hz line broadening, and referenced to an internal standard of 30 µM p-fluorophenylalanine (δ=−40.29 ppm). Data were processed using MestreC (NMR processing, analysis and simulation software by Mestrelab Research SL (Santiago de Compostela, SPAIN)).

Figure 5C:
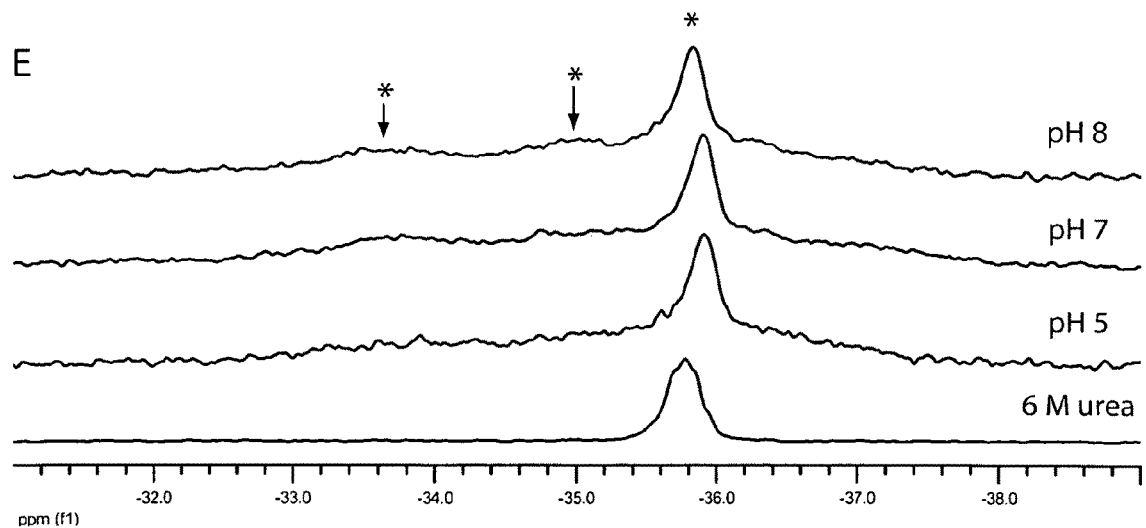

FIG. 5C shows the $^{19}$F-NMR spectra of 2-FHisPA$_{83}$ as a function of pH. It was assumed that any changes in the spectra of the protein as a function of pH in the range examined would be due to structural changes in the protein and not a result of protonation-deprotonation of 2-FHis itself, since the chemical shift of the amino acid does not change until very low pH values (see Yeh et al., *$^{19}$F and $^{1}$H nuclear magnetic resonance studies of ring-fluorinated imidazoles and histidines*, J. Chem. Soc. Perkin Trans. 2, 928-934 (1975)).

The spectra show several broad peaks (denoted with *), with one sharper peak (−35.8 ppm) that resonates at the same frequency as the unfolded resonance (6 M urea). The inability to resolve the 10 histidine residues is likely due to the slow tumbling of the 83 kD molecule, which results in longer transverse relaxation rates and broad resonances. However, the narrow −35.8 ppm resonance is likely attributable to a 2-FHis residue(s) in the transmembrane loop region that includes His304 and His310. This region is not resolved in crystal structures of full-length WT PA$_{83}$ and is expected to be mobile, and increase mobility as a function of decreasing pH. Consistent with a pH dependence on mobility in the transmembrane loop, there is a detectable upfield chemical shift change (Δδ0.08 ppm, 40 Hz) in this peak when the pH is lowered from 8 to 7, but no further changes down to pH 5.

Example 5

Trypsin Cleavage of PA$_{83}$

Conversion of PA$_{83}$ and 2-FHisPA$_{83}$ to the heptameric prepore (PA$_{63}$)$_7$ and (2-FHisPA$_{63}$)$_7$, respectively was performed at room temperature for 30 minutes by the addition of trypsin (Trypzean, Sigma-Aldrich) with a ratio of 1 µg of trypsin to 1 mg of PA$_{83}$, followed by the addition of a 10-fold excess of soybean trypsin inhibitor. Trypsin-activated PA was then loaded onto a Hi-Trap Q column equilibrated in 20 mM Tris, pH 8.5, and (PA$_{63}$)$_7$ or (2-FHisPA$_{63}$)$_7$ purified using a NaCl gradient (see Blaustein et al., *Anthrax Toxin: Channel-Forming Activity of Protective Antigen in Planar Phospholipid Bilayers*, Proc. Natl. Acad. Sci. 86 USA 2209-2213 (1989)). Final purification was accomplished by applying the preparation to a Sephadex S-200 gel filtration column (GE-Healthcare) equilibrated in 20 mM Tris-HCl, 400 mM NaCl, pH 8.5.

Example 6

Prepore to Pore Conversion of (PA$_{63}$)$_7$ and (2-FHisPA$_{63}$)$_7$

In this example, the ability of the 2-FHis labeled protein to carry out pore formation as a function of pH was investigated. The pH-dependent conversion of the heptamer (PA$_{63}$)$_7$ from a prepore to an SDS-resistant state was accomplished by incubating (PA$_{63}$)$_7$ (10 µL of 1.2 µM in 20 mM Tris-HCl pH 8.5, about 0.4 M NaCl) with 10 µL each of 1 M buffers (Bis-Tris, pH 5-6.5 and HEPES, pH 7-8) at room temperature for about one hour. After this incubation, 10% SDS was added to each sample to a final concentration of 1.25% SDS followed by incubation at room temperature for an additional 20 minutes. See Lacy et al., *Structure of heptameric protective antigen bound to an anthrax toxin receptor: A role for receptor in pH-dependent pore formation*, Proc. Natl. Acad. Sci. 101 USA 13147-13151 (2004). Proteins were then boiled for 5 minutes, and then applied to a 4-20% gradient SDS-PAGE gel which was run for about 3.5 hours at constant voltage (200V).

Figure 6A:
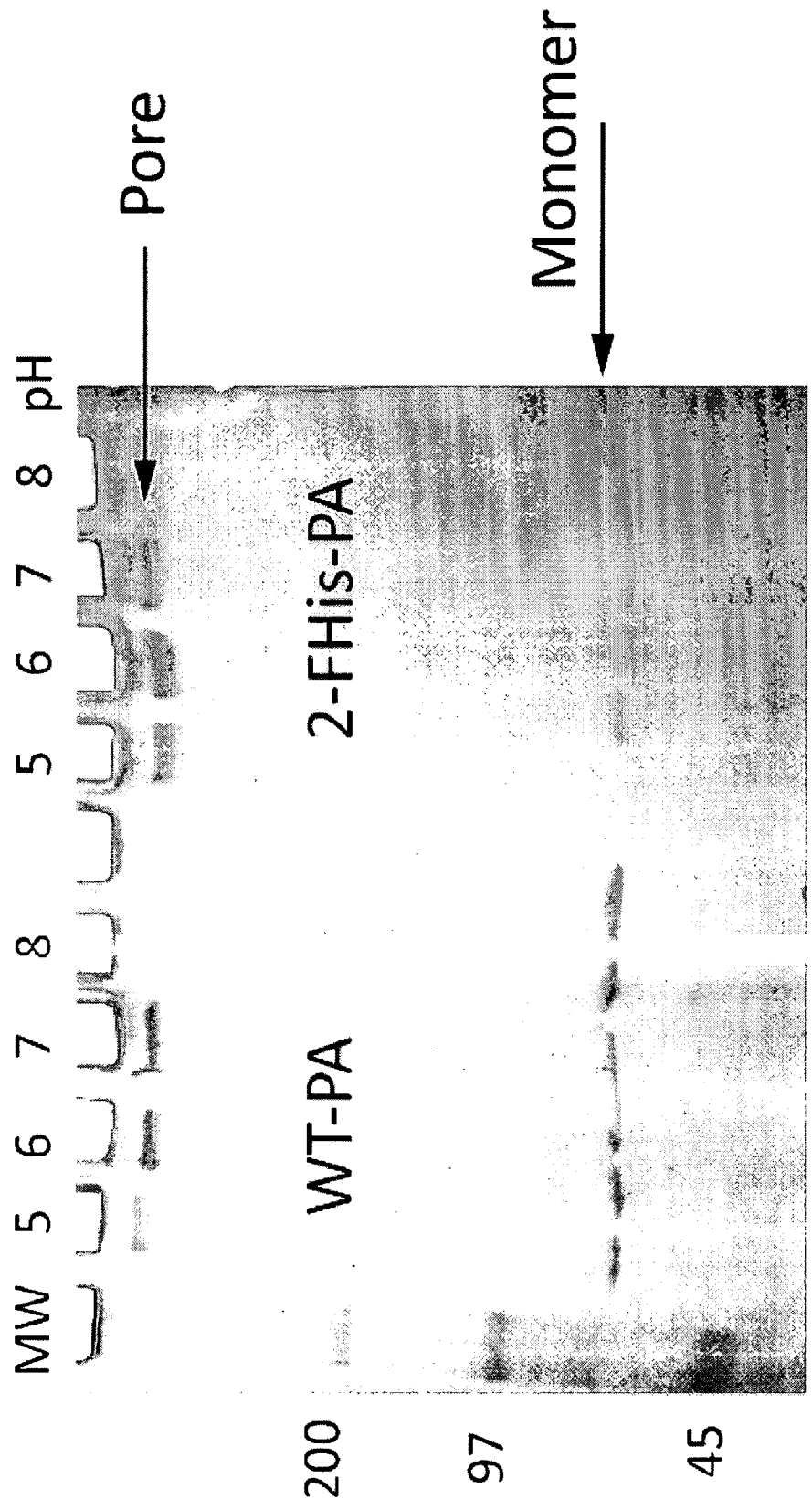
Figure 7:
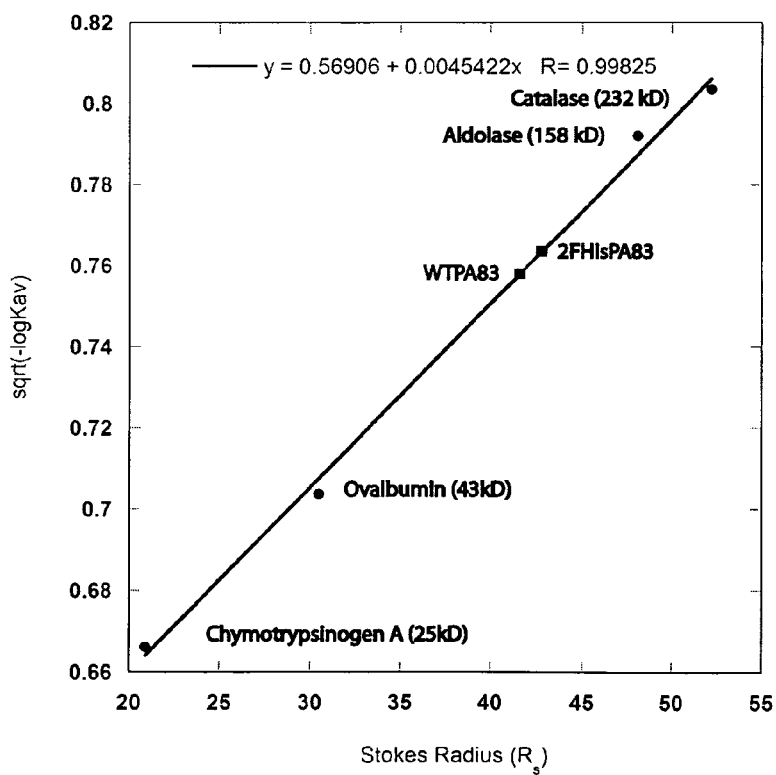
Figure 8A:
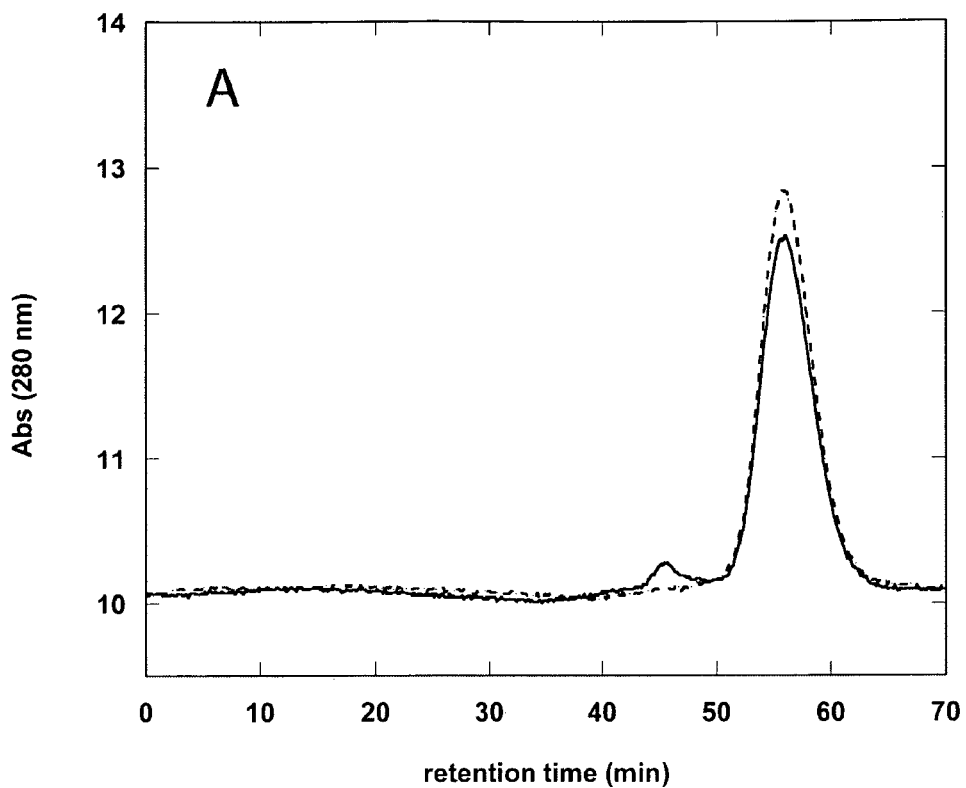
Figure 8B:
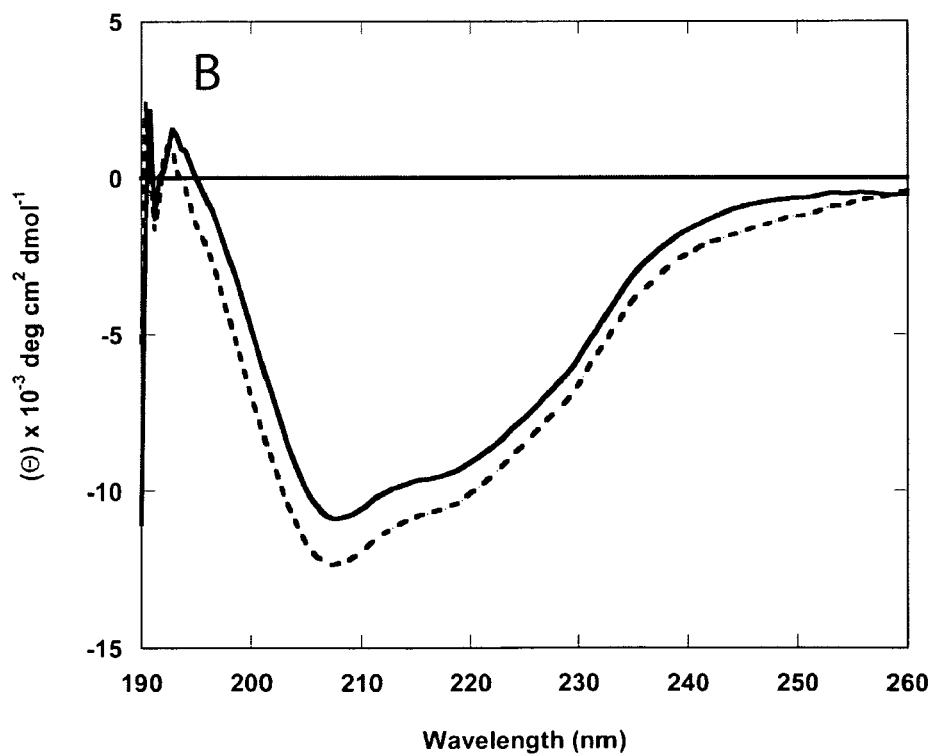

FIG. 6A shows the results for the prepore-pore conversion assayed by SDS-PAGE as a function of pH, and indicates that both proteins change to the pore conformation at similar pH values. Also, the structures of the two heptameric proteins are similar, since the far-UV CD spectra and the elution profiles from a Sephadex 200 gel filtration column of WT and 2-FHis labeled (PA$_{63}$)$_7$ overlapped (see FIG. 7). The data also suggest that the pH-dependent increase in stability observed for the full-length 2-FHisPA$_{83}$ (FIG. 4 and FIG. 5) is unable to attenuate pore formation for the (2-FHisPA$_{63}$)$_7$ complex.

Example 7

Pore Insertion into Membranes

In this example, the effect of 2-FHis on pore insertion into membranes was investigated. Membrane insertion of the pores was assayed using the potassium release (K$^+$ release) assay as previously described in Sun et al., *Insertion of Anthrax Protective Antigen into Liposomal Membranes: EFFECTS OF A RECEPTOR*, J. Biol. Chem. 282 1059-1065 (2007). Liposomes composed of 1,2-Dioleoyl-sn-glycerol-3-phosphocholine ("DOPC") were kindly provided by Dr. Jianjun Sun. Immediately prior to performing the K$^+$ release assay, the liposomes, maintained in a K⁺ buffer (10 mM HEPES, 100 mM KCl, pH 7.4) were buffer-exchanged into a Na⁺ buffer (10 mM HEPES, 100 mM NaCl, pH 7.4) in order to establish liposomes with K⁺ in the inside and Na⁺ on the outside. Purified $(PA_{63})_7$ or $(2\text{-FHisPA}_{63})_7$ heptamers (20 μg) in a buffer kept at pH 8.5 to maintain prepore state, were incubated with 150 μL of freshly prepared liposomes for 30 minutes on ice prior to being diluted into 5 ml of sodium acetate buffer, pH 5.0, containing 100 mM NaCl. Release of K⁺ from the liposomes was continuously monitored using a K⁺ selective electrode (Orion Research). Control (buffer alone) was subtracted from each experiment to allow comparison between different samples. The buffer-subtracted data from three experiments were averaged, and this data were fit to a sum of two exponentials using Kaleidagraph software.

Figure 6B:
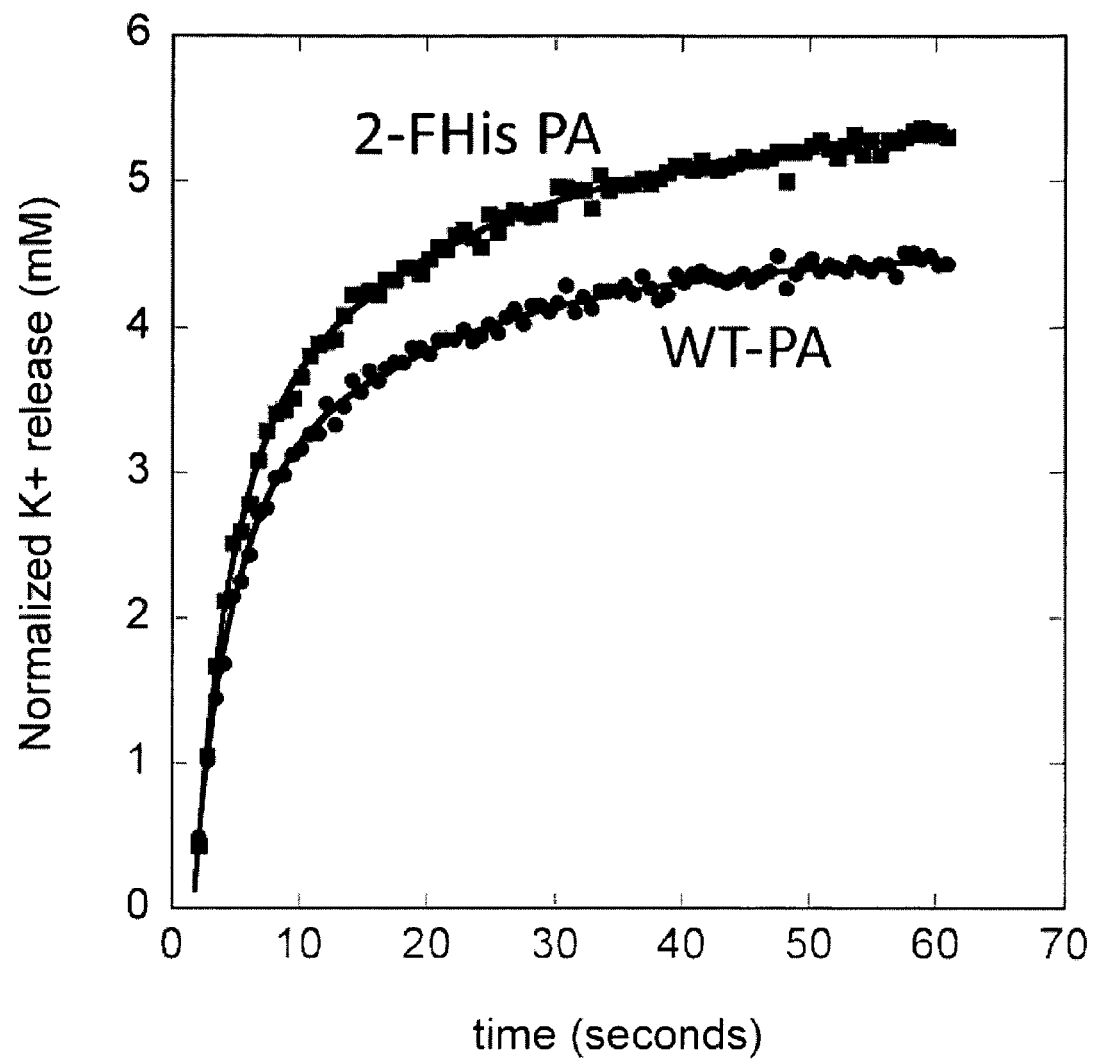

Both protein complexes released K⁺ from the liposomes at pH 5, suggesting that pores were formed, and this process occurred with similar biphasic rate constants ($k_1$=0.36 with +/−0.01 s⁻¹ (WT and 2-FHis); $k_2$=0.056+/−0.001 s⁻¹ (WT); $k_2$=0.053+/−0.001 s⁻¹ (2-FHis)) (FIG. 6B).

Example 8

Effect of 2-FHis on Translocation

In this example, translocation studies were carried out with a planar lipid bilayer system as described previously in Blaustein et al., *Anthrax Toxin: Channel-Forming Activity of Protective Antigen in Planar Phospholipid Bilayers*, Proc. Natl. Acad. Sci. 86 USA 2209-2213 (1989) and Takahashi et al., *Electrostatic forces in two lysozymes: Calculations and measurements of histidine pKa values*, Biopolymers 32 897-909 (1992). More specifically, $(PA_{63})_7$ or $(2\text{-FHisPA}_{63})_7$ was applied to the cis compartment, and changes in the macroscopic conductance of potassium across a membrane comprised of 3% 1,2-diphytanoyl-sn-glycerol-3-phosphocholine ("DPhPC") in n-decane (Avanti Polar Lipids, Alabaster, Ala.) were measured using a planar lipid bilayer workstation (Warner Instruments, Hamden, Conn.). Once channels started inserting at a faster rate, excess PA was actively removed using a syringe-mediated perfusion system at a rate of about 3 ml/min. After achieving a stable current, $LF_N$ (about 10 nM) was added to the cis compartment, and blockage of channel conductance was measured. Excess $LF_N$ was removed by perfusing with 10 ml of buffer and then translocation was initiated by increasing ΔΨ to +30 mV or by a change in pH of the trans compartment to pH 7.4 from pH 5.5 by the addition of KOH. See Krantz et al., *A Phenylalanine Clamp Catalyzes Protein Translocation Through the Anthrax Toxin Pore*, Science 309 777-781 (2005). Data were analyzed using AxographX (AxoGraph Scientific, Sydney, Australia).

Figure 6C:
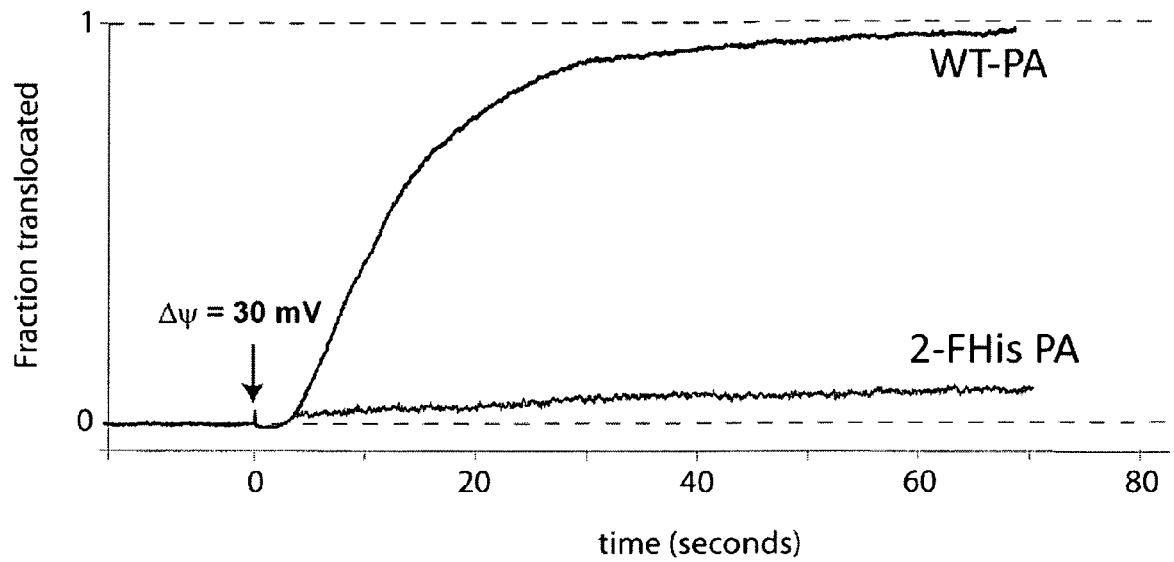

In planar lipid bilayers formed from DPhPC, $LF_N$ bound to both $(PA_{63})_7$ and $(2\text{-FHisPA}_{63})_7$ pores, blocking channel conductance by more than 95%. For the WT protein, application of either a change in voltage to a positive membrane potential (from +20 mV to +50 mV, ΔΨ=+30 mV), or increasing the pH of the trans side, drives $LF_N$ through the pore (the cis side of the membrane is the side to which $PA_{63}$ and $LF_N$ are added). The $(2\text{-FHisPA}_{63})_7$ formed heptameric channels similar to the WT protein, and in the presence of $LF_N$ these channels were blocked, indicating that the binding surfaces necessary for entry of $LF_N$ into the pore were not perturbed. However, neither increasing the membrane potential to 30 mV (FIG. 6C) nor a raising of one pH in the trans compartment (data not shown) was sufficient to drive $LF_N$ through these pores.

Example 9

Protein Synthesis Experiments in CHO-K1 Cells

Since the translocation experiments indicated that the 2-FHis labeled protein was unable to carry out translocation in vitro, this suggested that it would also not function in mediating cellular cytotoxicity. In order to determine if the $2\text{-FHisPA}_{83}$ is functional in cells, a cytotoxicity assay was used where $2\text{-FHis PA}_{83}$ is added to CHO-K1 cells along with $LF_N$-DTA, a fusion of $LF_N$ and the catalytic domain of diphtheria toxin, which once inside the cell inhibits protein synthesis. See Krantz et al., *A Phenylalanine Clamp Catalyzes Protein Translocation Through the Anthrax Toxin Pore*, Science 309 777-781 (2005); Sellman et al., *Dominant-Negative Mutants of a Toxin Subunit: An Approach to Therapy of Anthrax*, Science 292 695-697 (2001). CHO-K1 cells contain on their surfaces the ANTXR2 receptor and the furin-like protease to cleave $PA_{83}$ to $PA_{20}$ and $PA_{63}$, uptake $(PA_{63})_7$-$LF_N$-DTA, and once pore formation occurs, translocate $LF_N$-DTA into the cytosol. This results eventually in a loss in protein synthesis as assayed by incorporation of ³H-leucine into cells.

Translocation studies in CHO-K¹ cells were conducted in 96-well microtiter plates. CHO-K1 cells were incubated with wild-type or $2\text{-FHisPA}_{83}$, in the presence of $LF_N$ fused with the catalytic subunit of diphtheria toxin ($LF_N$-DTA) for 4 hours at 37° C. Medium was removed and replaced with leucine-free HAM F-12 supplemented with ³H-Leucine. After incubation for one hour at 37° C., cells were washed with PBS and then incubated with ice cold 10% trichloroacetic acid. The ability of DTA to block protein synthesis was quantified by measuring the amount of ³H-leucine present in the TCA precipitate. The amount incorporated in the absence of $PA_{83}$ (and thus no diphtheria toxin) was compared to that in the presence of wild-type $PA_{83}$ as well as the 2-FHis labeled counterparts.

Figure 2:
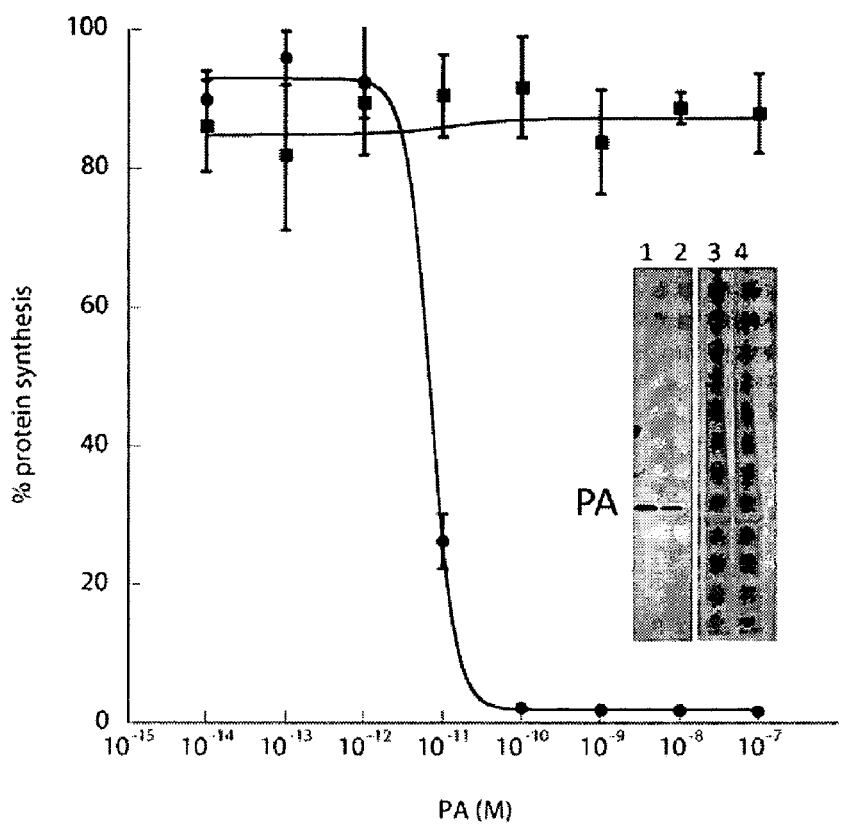

In contrast to results with $(PA_{63})_7$-$LF_N$-DTA (FIG. 6A), no inhibition of protein synthesis was detected after addition of $2\text{-FHisPA}_{83}$/$LF_N$-DTA to CHO-K1 cells (FIG. 2).

Example 10

Block in Pore Formation in the Presence of the VWA Domain of ANTXR2

In preliminary experiments, $(2\text{-FHisPA}_{63})_7$ is unable to undergo pH dependent pore formation in the presence of ANTXR2. Cultures of the *E. coli* strain BL21-DE3 harboring pGEX-4T1-ANTRX2³⁸⁻²¹⁸ in Luria-Bertani media were grown to an $A_{600}$ of 1.0, and induced for 3 hours at 37° C. The cells were collected and resuspended in a small volume (about 20 ml) of ice-cold phosphate buffered saline (PBS) pH 7.2. Lysozyme (hen egg white) was added to a final concentration of 1 mg/ml, and the cells were incubated on ice for 30 minutes. The cells were then lysed using a sonicator, and subsequently centrifuged (8000×g), and the supernatant applied to a 5×5 ml glutathione-sepharose HP column (GE HealthCare) equilibrated in PBS. Elution of the protein was achieved by using thrombin (80 Units/ml resin) to cleave between ANTRX2 and glutathione followed by passing the preparation through a 5×5 ml benzamidine column (GE-Healthcare), affording pure VWA domain of ANTXR2. Concentrations were determined using an extinction coefficient of 13,200 M⁻¹cm⁻¹.

Prepore to pore conversion for both the WT and (2-FHis PA$_{63}$)$_7$ in the presence of the VWA domain of ANTXR2 were examined using SDS-PAGE (FIG. 9). In these experiments, 0.9 µM PA$_{63}$ in 20 mM Tris-HCl pH 8.5 and 5 µM ANTRX2 in PBS were mixed, and diluted into buffers (350 mM final): BisTris (pH 5 and 6) and HEPES (pH 7 and 8). While the pH dependent prepore to pore conversion for WT heptamer in the presence of ANTRX2 occurs at pH 6, the (2-FHisPA$_{63}$)$_7$ does not undergo pore formation at any of the lower pH values.

Together, the foregoing examples show that the pH-dependent conversion of anthrax PA$_{83}$ from a heptameric prepore to a functional pore is a key step in the pathogenic mechanism of the toxin. The pKa of histidine is about 6, and because of the prevalence of histidines in PA, particularly in domain 2 and the transmembrane loop, it was theorized that histidine protonation at reduced pH may trigger the prepore to pore conversion. When PA$_{83}$ was labeled with 2-FHis, an isosteric analog of histidine with a pKa of about 1, the full-length 2-FHisPA$_{83}$ protein exhibited a similar structure and stability to the WT protein. However, the stability to pH is increased. The increased stability to pH was likely due to an influence on the protonation state of histidine residues in domains 2 to 4 because the stability to pH of domain 1 seems largely unaffected by 2-FHis labeling. Also, the increased stability to pH is not likely due to an effect of the fluorine atom on local side-chain hydrophobicity, since no change was observed in the stability of the protein to urea where this effect is normally resolved. Despite an increased stability to pH for the full-length 2-FHisPA$_{83}$, however, the heptameric (2-FHisPA$_{63}$)$_7$ retained the ability to undergo pore formation at pH values similar to the WT protein. The (2-FHisPA$_{63}$)$_7$ can also insert into membranes and form ion conducting channels. However, translocation of LF$_N$, the N-terminal PA binding domain of lethal factor (LF), and a fusion of LF$_N$ and diphtheria toxin (LF$_N$-DTA), was blocked.

The references cited herein, as well as the following references, to the extent that they provide exemplary procedural or other details supplementary to those herein, are incorporated herein by reference.

Abrami et al., *Anthrax toxin triggers endocytosis of its receptor via a lipid raft-mediated clathrin-dependent process*, J. Cell Biol. 160, 321-328 (2003).

Bradley et al., *Identification of the cellular receptor for anthrax toxin*, Nature. 414, 225-229 (2001).

Bell et al., *Differential gene expression during capillary morphogenesis in 3D collagen matrices: regulated expression of genes involved in basement membrane matrix assembly, cell cycle progression, cellular differentiation and G-protein signaling*, J. Cell Science, 114 2755-2773 (2001).

Christensen et al., *Interaction of the 20 kDa and 63 kDa fragments of anthrax protective antigen: kinetics and thermodynamics*, Biochemistry 44 1047-1053 (2005).

Collier et al., *Anthrax toxin*, Annu. Rev. Cell Dev. Biol. 19 45-70 (2003).

Lacy et al., *Structure of heptameric protective antigen bound to an anthrax toxin receptor: A role for receptor in pH-dependent pore formation*, Proc. Natl. Acad. Sci. 101 USA 13147-13151 (2004).

Lacy et al., *A model of anthrax toxin lethal factor bound to protective antigen*, Proc. Natl. Acad. Sci. USA 102 16409-16414 (2005).

Perier et al., *Concerted Protonation of Key Histidines Triggers Membrane Interaction of the Diphtheria Toxin T Domain*, J. Biol. Chem. 282 24239-24245 (2007).

Sellman et al., *Point Mutations in Anthrax Protective Antigen That Block Translocation*, J. Biol. Chem. 276 8371-8376 (2001).

Scobie et al., *Human capillary morphogenesis protein 2 functions as an anthrax toxin receptor*, Proc. Natl. Acad. Sci. USA 100 5170-5174 (2003).

Melnyk et al., *Structural Determinants for the Binding of Anthrax Lethal Factor to Oligomeric Protective Antigen*, J. Biol. Chem. 281 1630-1635 (2006).

Wei et al., *The LDL Receptor-Related Protein LRP6 Mediates Internalization and Lethality of Anthrax Toxin*, Cell. 124 1141-1154 (2006).

Nassi et al., *PA$_{63}$ Channel of Anthrax Toxin: An Extended β-Barrel*, Biochemistry 41 1144-1450 (2002).

Benson et al., *Identification of Residues Lining the Anthrax Protective Antigen Channel*, Biochemistry 37 3941-3948 (1998).

Miller et al., *Anthrax Protective Antigen: Prepore-to Pore Conversion*, Biochemistry 38(32) 10432-10441 (1999).

Blaustein et al., *Anthrax Toxin: Channel-Forming Activity of Protective Antigen in Planar Phospholipid Bilayers*, Proc. Natl. Acad. Sci. 86 USA 2209-2213 (1989).

Takahashi et al., *Electrostatic forces in two lysozymes: Calculations and measurements of histidine pKa values*, Biopolymers 32 897-909 (1992).

Singer et al., *pH Titration studies of an SH2 domain-phosphopeptide complex: Unusual histidine and phosphate pK(a) values*, Protein Science 6 1910-1919 (1997).

Santelli et al., *Crystal structure of a complex between anthrax toxin and its host cell receptor*, Nature. 430 905-908 (2004).

Minks et al., *Atomic mutations at the single tryptophan residue of human recombinant annexin V: Effects on structure, stability and activity*, Biochemistry 38 10649-10659 (1999).

Son, S. I., Caglar, T., and Tirrell, D. A., ChemBioChem. 7, 1-8 (2006).

Eichler et al., *Biosynthetic Incorporation of Fluorohistidine into Proteins in E. coli: A New Probe of Macromolecular Structure*, ChemBioChem 6 1-4 (2005).

Kirk et al., *Photochemistry of diazonium salts. I. Synthesis of 4-Fluoroimidazoles, 4-Fluorohistamine, and 4-Fluorohistinine*, J. Amer. Chem. Soc. 38 4619-4624 (1972).

Kirk et al., *Photochemistry of diazonium salts. II. Synthesis of 2-fluoro-L-histidine and 2-fluorohistamine, and the halogen lability of 2-fluoroimidazoles*, J. Amer Chem. Soc. 95 8389-8392 (1973).

Yeh et al., *$^{19}$F and $^1$H nuclear magnetic resonance studies of ring-fluorinated imidazoles and histidines*, J. Chem. Soc. Perkin Trans. 2 928-934 (1975).

Panasik et al., *Inductive effects on the structure of proline residues*, Int. J. Pept. Prot. Sci. 44 262-269 (1994).

Wigelsworth et al., *Binding Stoichiometry and Kinetics of the Interaction of a Human Anthrax Toxin Receptor, CMG2, with Protective Antigen*, J. Biol. Chem. 279 23349-23356 (2004).

Frieden et al., *The preparation of 19F-labeled proteins for NMR studies*, Methods Enzymol. 380 400-415 (2004).

Pace et al., *How to measure and predict the molar absorption coefficient of a protein*, Protein Sci. 11 2411-2423 (1995).

Barrick et al., *A three-state analysis of apomyoglobin unfolding*, Biochemistry 32 3790-3796 (1993).

Tan et al., *Contributions of a Highly Conserved V$_H$/V$_L$ Hydrogen Bonding Interaction to scFv Folding Stability and Refolding Efficiency*, Biophysical Journal 75 1473-1482 (1998).

Goldenberg, *Protein Structure: A Practical Approach, 2$^{nd}$ ed.* (Ed.: T. E. Creighton) Oxford University Press, Oxford, U.K (1997).

MestreC: NMR processing, analysis and simulation software by MESTRELAB RESEARCH SL (Santiago de Compostela, SPAIN)(www.mestrec.com).

Sun et al., *Insertion of Anthrax Protective Antigen into Liposomal Membranes: Effects of A Receptor*, J. Biol. Chem. 282 1059-1065 (2007).

Krantz et al., *A Phenylalanine Clamp Catalyzes Protein Translocation Through the Anthrax Toxin Pore*, Science 309 777-781 (2005).

Sellman et al., *Dominant-Negative Mutants of a Toxin Subunit: An Approach to Therapy of Anthrax*, Science 292 695-697 (2001).

Yan et al., *Characterization of Dominant-Negative Forms of Anthrax Protective Antigen*, Mol. Medicine. 9 46-51 (2003).

Gupta et al., *Conformational fluctuations in anthrax protective antigen: a possible role of calcium in the folding pathway of the protein*, FEBS Letters 554 505-510 (2003).

Barrick et al., *Molecular Mechanisms of Acid Denaturation: The Role of Histidine Residues in the Partial Unfolding of Apomyoglobin*, J. Mol. Biol. 237 588-601 (1994).

Petosa et al., *Crystal structure of a complex between anthrax toxin and its host cell receptor*, Nature. 430 905-908 (2004).

Krantz et al., *Protein translocation through the anthrax toxin transmembrane pore is driven by a proton gradient*, J. Mol. Biol. 355 968-979 (2006).

Rainey et al., *Receptor-specific requirements for anthrax toxin delivery into cells*, Proc. Natl. Acad. Sci. USA 102 13278-13283 (2005).

Mourez et al., *Mapping dominant-negative mutations of anthrax protective antigen by scanning mutagenesis*, Proc. Natl. Acad. Sci. USA 100 13803-13808 (2003).

Panchal et al., *Interactions between Residues in Staphylococcal-Hemolysin Revealed by Reversion Mutagenesis*, J. Biol. Chem. 270 23072-23076 (1995).

Christensen, *Interaction of the 20 kDa and 63 kDa fragments of anthrax protective antigen: kinetics and thermodynamics*, Biochemistry 44 1047-1053 (2005).

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A protective antigen protein having a modified histidine residue with a fluorine at the 2-position so that the pKa of the modified histidine residue is less than about 3.

2. The protective antigen protein of claim 1 wherein at least 50% of the histidine residues are modified to have a pKa of less than about 3.

3. The protective antigen protein of claim 1 wherein at least 90% of the histidine residues are modified to have a pKa of less than about 3.

4. The protective antigen protein of claim 1 wherein said modified histidine residue has a pKa of about 1.

5. A pharmaceutical composition comprising the protective antigen protein of claim 1 and a pharmaceutical carrier.

6. The pharmaceutical composition of claim 5 further comprising an agent selected from the group consisting an antibody against lethal factor, an antibody against edema factor, and antibody against protective antigen, ciprofloxacin, doxycycline, chloramphenicol, clindamycin, tetracycline, rifampin, and vancomycin.

* * * * *